US008465957B2

(12) United States Patent
Svendsen et al.

(10) Patent No.: US 8,465,957 B2
(45) Date of Patent: *Jun. 18, 2013

(54) ALPHA-AMYLASE VARIANTS

(75) Inventors: Allan Svendsen, Birkeroed (DK); Soren Kjaerulff, Vanlose (DK); Henrik Bisgaard-Frantzen, Bagsvaerd (DK); Carsten Andersen, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/478,512

(22) Filed: May 23, 2012

(65) Prior Publication Data

US 2012/0252095 A1     Oct. 4, 2012

Related U.S. Application Data

(60) Division of application No. 13/038,991, filed on Mar. 2, 2011, now abandoned, which is a division of application No. 12/417,453, filed on Apr. 2, 2009, now abandoned, which is a division of application No. 11/039,565, filed on Jan. 19, 2005, now Pat. No. 7,601,527, which is a continuation of application No. 09/441,313, filed on Nov. 16, 1999, now Pat. No. 6,887,986, which is a continuation-in-part of application No. 09/193,068, filed on Nov. 16, 1998, now Pat. No. 6,197,565.

(51) Int. Cl.
*C12N 9/28*     (2006.01)

(52) U.S. Cl.
USPC ........... 435/202; 435/204; 435/210; 510/226; 510/236; 510/530; 510/320; 510/392

(58) Field of Classification Search
None
See application file for complete search history.

(56) References Cited

U.S. PATENT DOCUMENTS

| 5,731,280 | A | 3/1998 | Nielsen et al. |
| 5,989,169 | A | 11/1999 | Svendsen et al. |

FOREIGN PATENT DOCUMENTS

| WO | WO 90/11352 | 10/1990 |
| WO | WO 95/10603 | 4/1995 |
| WO | WO 95/26397 | 10/1995 |
| WO | WO 96/23873 | 8/1996 |
| WO | WO 96/23874 | 8/1996 |
| WO | WO 97/41213 | 11/1997 |
| WO | WO 97/43424 | 11/1997 |
| WO | WO 98/26078 | 6/1998 |
| WO | WO 99/19467 | 4/1999 |

OTHER PUBLICATIONS

Beaucage et al., Tetrahedron Lett., vol. 22, No. 20, pp. 1859-1862 (1981).
Boel et al., Biochemistry, vol. 29, pp. 6244-6249 (1990).
Brady et al., Acta Cryst., vol. 47, pp. 527-535 (1991).
Chang et al., J. Mol. Biol., vol. 229, pp. 235-238 (1993).
Conrad et al., Eur. J. Biochem., vol. 230, pp. 481-490 (1995).
Diderichsen et al., FEMS Microbiol. Lett., vol. 56, pp. 53-60 (1988).
Dubnau et al., J. Mol. Biol., vol. 56, pp. 209-221 (1971).
Erlich, Proc. Natl. Acad. Sci. USA, vol. 74, pp. 1680-1682 (1977).
Gryczan et al., J. Bacteriol., vol. 134, No. 1, pp. 318-329 (1978).
Higuchi et al., Nucleic Acids Res., vol. 16, No. 15, pp. 7351-7367 (1988).
Hunkapiller et al., Nature, vol. 310, pp. 105-111 (1984).
Kadziola, Thesis on "An Alpha-Amylase From Barley and Its Complex With a Substrate Analogue Inhibitor Studied by X-Ray Crystallography" (1993).
Klein et al., Biochemistry, vol. 31, pp. 8740-8746 (1992).
Larson et al., J. Mol. Biol., vol. 235, pp. 1560-1584 (1994).
Lawson et al., J. Mol. Biol., vol. 236, pp. 590-600 (1994).
MacGregor, Food Hydrocol., vol. 1, No. 5-6, pp. 407-411 (1987).
Matthes et al., EMBO J., vol. 3, No. 4, pp. 801-805 (1984).
Mizuno et al., J. Mol. Biol., vol. 234, pp. 1282-1283 (1993).
Morinaga et al., Biotechnology, vol. 2, pp. 636-646 (1984).
Nelson et al., Anal. Biochem., vol. 180, pp. 147-151 (1989).
Ngo et al., The Protein Folding Problem and Tertiary Structure Prediction, p. 433 (1994).
Ngo et al., The Protein Folding Problem and Tertiary Structure Prediction, pp. 492-506 (1994).
Qian et al., J. Mol. Biol., vol. 231, pp. 785-799 (1993).
Saiki et al., Science, vol. 239, pp. 487-491 (1988).
Swift et al., Acta Cryst., vol. 47, pp. 535-544 (1991).

*Primary Examiner* — Richard Hutson
(74) *Attorney, Agent, or Firm* — Michael W. Krenicky

(57) ABSTRACT

The invention relates to a variant of a parent Termamyl-like alpha-amylase, comprising mutations in two, three, four, five or six regions/positions. The variants have increased stability at high temperatures (relative to the parent). The invention also relates to a DNA construct comprising a DNA sequence encoding an alpha-amylase variant of the invention, a recombinant expression vector which carries a DNA construct of the invention, a cell which is transformed with a DNA construct of the invention, the use of an alpha-amylase variant of the invention for washing and/or dishwashing, textile desizing, starch liquefaction, a detergent additive comprising an alpha-amylase variant of the invention, a manual or automatic dishwashing detergent composition comprising an alpha-amylase variant of the invention, a method for generating a variant of a parent Termamyl-like alpha-amylase, which variant exhibits increased.

6 Claims, 4 Drawing Sheets

```
     1                                                                50
1    HHNGTNGTMM QYFEWHLPND GNHWNRLRDD ASNLRNRGIT AIWIPPAWKG
2    ..NGTNGTMM QYFEWYLPND GNHWNRLRSD ASNLKDKGIS AVWIPPAWKG
3    HHNGTNGTMM QYFEWYLPND GNHWNRLRDD AANLKSKGIT AVWIPPAWKG
4    ....VNGTLM QYFEWYTPND GQHWKRLQND AEHLSDIGIT AVWIPPAYKG
5    ..ANLNGTLM QYFEWYMPND GQHWRRLQND SAYLAEHGIT AVWIPPAYKG
6    .AAPFNGTMM QYFEWYLPDD GTLWTKVANE ANNLSSLGIT ALWLPPAYKG 51                                                               100
1    TSQNDVGYGA YDLYDLGEFN QKGTVRTKYG TRSQLESAIH ALKNNGVQVY
2    ASQNDVGYGA YDLYDLGEFN QKGTIRTKYG TRNQLQAAVN ALKSNGIQVY
3    TSQNDVGYGA YDLYDLGEFN QKGTVRTKYG TRNQLQAAVT SLKNNGIQVY
4    LSQSDNGYGP YDLYDLGEFQ QKGTVRTKYG TKSELQDAIG SLHSRNVQVY
5    TSQADVGYGA YDLYDLGEFH QKGTVRTKYG TKGELQSAIK SLHSRDINVY
6    TSRSDVGYGV YDLYDLGEFN QKGTVRTKYG TKAQYLQAIQ AAHAAGMQVY 101                                                              150
1    GDVVMNHKGG ADATENVLAV EVNPNNRNQE ISGDYTIEAW TKFDFPGRGN
2    GDVVMNHKGG ADATEMVRAV EVNPNNRNQE VSGEYTIEAW TKFDFPGRGN
3    GDVVMNHKGG ADGTEIVNAV EVNRSNRNQE TSGEYAIEAW TKFDFPGRGN
4    GDVVLNHKAG ADATEDVTAV EVNPANRNQE TSEEYQIKAW TDFRFPGRGN
5    GDVVINHKGG ADATEDVTAV EVDPADRNRV ISGEHLIKAW THFHFPGRGS
6    ADVVFDHKGG ADGTEWVDAV EVNPSDRNQE ISGTYQIQAW TKFDFPGRGN 151                                                              200
1    TYSDFKWRWY HFDGVDWDQS RQFQNRIYKF RGDGKAWDWE VDSENGNYDY
2    THSNFKWRWY HFDGVDWDQS RKLNNRIYKF RGDGKGWDWE VDTENGNYDY
3    NHSSFKWRWY HFDGTDWDQS RQLQNKIYKF RGTGKAWDWE VDTENGNYDY
4    TYSDFKWHWY HFDGADWDES RKI.SRIFKF RGEGKAWDWE VSSENGNYDY
5    TYSDFKWHWY HFDGTDWDES RKL.NRIYKF ..QGKAWDWE VSNENGNYDY
6    TYSSFKWRWY HFDGVDWDES RKL.SRIYKF RGIGKAWDWE VDTENGNYDY
```

Figure 1

```
      201                                                          250
1     LMYADVDMDH PEVVNELRRW GEWYTNTLNL DGFRIDAVKH IKYSFTRDWL
2     LMYADIDMDH PEVVNELRNW GVWYTNTLGL DGFRIDAVKH IKYSFTRDWS
3     LMYADVDMDH PEVIHELRNW GVWYTNTLNL DGFRIDAVKH IKYSFTRDWL
4     LMYADVDYDH PDVVAETKKW GIWYANELSL DGFRIDAAKH IKFSFLRDWV
5     LMYADIDYDH PDVAAEIKRW GTWYANELQL DGFRLDAVKH IKFSFLRDWV
6     LMYADLDMDH PEVVTELKNW GKWYVNTTNI DGFRLDAVKH IKFSFFPDWL 251                                                          300
1     THVRNATGKE MFAVAEFWKN DLGALENYLN KTNWNHSVFD VPLHYNLYNA
2     IHVRSATGKN MFAVAEFWKN DLGAIENYLN KTNWNHSVFD VPLHYNFYNA
3     THVRNTTGKP MFAVAEFWKN DLGAIENYLN KTSWNHSAFD VPLHYNLYNA
4     QAVRQATGKE MFTVAEYWQN NAGKLENYLN KTSFNQSVFD VPLHFNLQAA
5     NHVREKTGKE MFTVAEYWQN DLGALENYLN KTNFNHSVFD VPLHYQFHAA
6     SYVRSQTGKP LFTVGEYWSY DINKLHNYIT KTDGTMSLFD APLHNKFYTA 301                                                          350
1     SNSGGNYDMA KLLNGTVVQK HPMHAVTFVD NHDSQPGESL ESFVQEWFKP
2     SKSGGNYDMR QIFNGTVVQR HPMHAVTFVD NHDSQPEEAL ESFVEEWFKP
3     SNSGGYYDMR NILNGSVVQK HPTHAVTFVD NHDSQPGEAL ESFVQQWFKP
4     SSQGGGYDMR RLLDGTVVSR HPEKAVTFVE NHDTQPGQSL ESTVQTWFKP
5     STQGGGYDMR KLLNGTVVSK HPLKSVTFVD NHDTQPGQSL ESTVQTWFKP
6     SKSGGAFDMR TLMTNTLMKD QPTLAVTFVD NHDTEPGQAL QSWVDPWFKP 351                                                          400
1     LAYALILTRE QGYPSVFYGD YYGIPTHS.. .VPAMKAKID PILEARQNFA
2     LAYALTLTRE QGYPSVFYGD YYGIPTHG.. .VPAMKSKID PILEARQKYA
3     LAYALVLTRE QGYPSVFYGD YYGIPTHG.. .VPAMKSKID PLLQARQTFA
4     LAYAFILTRE SGYPQVFYGD MYGTKGTSPK EIPSLKDNIE PILKARKEYA
5     LAYAFILTRE SGYPQVFYGD MYGTKGDSQR EIPALKHKIE PILKARKQYA
6     LAYAFILTRQ EGYPCVFYGD YYGIPQYN.. .IPSLKSKID PLLIARRDYA 401                                                          450
1     YGTQHDYFDH HNIIGWTREG NTTHPNSGLA TIMSDGPGGE KWMYVGQNKA
2     YGRQN..... .......... .......... .......... ..........
3     YGTQHDYFDH HDIIGWTREG NSSHPNSGLA TIMSDGPGGN KWMYVGKNKA
4     YGPQHDYIDH PDVIGWTREG DSSAAKSGLA ALITDGPGGS KRMYAGLKNA
5     YGAQHDYFDH HDIVGWTREG DSSVANSGLA ALITDGPGGA KRMYVGRQNA
6     YGTQHDYLDH SDIIGWTREG GTEKPGSGLA ALITDGPGGS KWMYVGKQHA
```

Figure 1 (continued)

```
      451                                                         500
1  GQVWHDITGN KPGTVTINAD GWANFSVNGG SVSIWVKR.. ..........
2  .......... .......... .......... .......... ..........
3  GQVWRDITGN RTGTVTINAD GWGNFSVNGG SVSVWVKQ.. ..........
4  GETWYDITGN RSDTVKIGSD GWGEFHVNDG SVSIYVQ... ..........
5  GETWHDITGN RSEPVVINSE GWGEFHVNGG SVSIYVQR.. ..........
6  GKVFYDLTGN RSDTVTINSD GWGEFKVNGG SVSVWVPRKT TVSTIARPIT 501                519
1  .......... ..........
2  .......... ..........
3  .......... ..........
4  .......... ..........
5  .......... ..........
6  TRPWTGEFVR WTEPRLVAW
```

Figure 1 (continued)

SEQUENCE LISTING

<160> NUMBER OF SEQ ID NOS: 32

<210> SEQ ID NO 1
<211> LENGTH: 485
<212> TYPE: PRT
<213> ORGANISM: Bacillus

<400> SEQUENCE: 1

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
        355                 360                 365
```

Gly Asp Tyr Tyr Gly Ile Pro Thr His Gly Val Pro Ala Met Lys Ser
370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
        435                 440                 445

Gln Val Trp Arg Asp Ile Thr Gly Asn Arg Thr Gly Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
            485

<210> SEQ ID NO 2
<211> LENGTH: 485
<212> TYPE: PRT
<213> ORGANISM: Bacillus

<400> SEQUENCE: 2

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

```
Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 3
<211> LENGTH: 514
<212> TYPE: PRT
<213> ORGANISM: Bacillus stearothermophilus

<400> SEQUENCE: 3

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140
```

```
Pro Gly Arg Gly Asn Thr Tyr Ser Ser Phe Lys Trp Arg Trp Tyr His
145                 150                 155                 160

Phe Asp Gly Val Asp Trp Asp Glu Ser Lys Leu Ser Arg Ile Tyr
            165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Ser Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
            245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
            275                 280                 285

Ala Pro Leu His Asn Lys Phe Tyr Thr Ala Ser Lys Ser Gly Gly Thr
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
            325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
            405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
            485                 490                 495

Arg Pro Trp Thr Asp Glu Phe Val Arg Trp Thr Glu Pro Arg Leu Val
            500                 505                 510

Ala Trp

<210> SEQ ID NO 4
<211> LENGTH: 483
<212> TYPE: PRT
<213> ORGANISM: Bacillus licheniformis
```

<400> SEQUENCE: 4

| Ala | Asn | Leu | Asn | Gly | Thr | Leu | Met | Gln | Tyr | Phe | Glu | Trp | Tyr | Met | Pro |
| 1 | | | | 5 | | | | | 10 | | | | | 15 | |

| Asn | Asp | Gly | Gln | His | Trp | Arg | Arg | Leu | Gln | Asn | Asp | Ser | Ala | Tyr | Leu |
| | | | 20 | | | | | 25 | | | | | 30 | | |

| Ala | Glu | His | Gly | Ile | Thr | Ala | Val | Trp | Ile | Pro | Pro | Ala | Tyr | Lys | Gly |
| | | 35 | | | | | 40 | | | | | 45 | | | |

| Thr | Ser | Gln | Ala | Asp | Val | Gly | Tyr | Gly | Ala | Tyr | Asp | Leu | Tyr | Asp | Leu |
| | 50 | | | | | 55 | | | | | 60 | | | | |

| Gly | Glu | Phe | His | Gln | Lys | Gly | Thr | Val | Arg | Thr | Lys | Tyr | Gly | Thr | Lys |
| 65 | | | | | 70 | | | | | 75 | | | | | 80 |

| Gly | Glu | Leu | Gln | Ser | Ala | Ile | Lys | Ser | Leu | His | Ser | Arg | Asp | Ile | Asn |
| | | | | 85 | | | | | 90 | | | | | 95 | |

| Val | Tyr | Gly | Asp | Val | Val | Ile | Asn | His | Lys | Gly | Gly | Ala | Asp | Ala | Thr |
| | | | 100 | | | | | 105 | | | | | 110 | | |

| Glu | Asp | Val | Thr | Ala | Val | Glu | Val | Asp | Pro | Ala | Asp | Arg | Asn | Arg | Val |
| | | | 115 | | | | | 120 | | | | | 125 | | |

| Ile | Ser | Gly | Glu | His | Leu | Ile | Lys | Ala | Trp | Thr | His | Phe | His | Phe | Pro |
| | 130 | | | | | 135 | | | | | 140 | | | | |

| Gly | Arg | Gly | Ser | Thr | Tyr | Ser | Asp | Phe | Lys | Trp | His | Trp | Tyr | His | Phe |
| 145 | | | | | 150 | | | | | 155 | | | | | 160 |

| Asp | Gly | Thr | Asp | Trp | Asp | Glu | Ser | Arg | Lys | Leu | Asn | Arg | Ile | Tyr | Lys |
| | | | | 165 | | | | | 170 | | | | | 175 | |

| Phe | Gln | Gly | Lys | Ala | Trp | Asp | Trp | Glu | Val | Ser | Asn | Glu | Asn | Gly | Asn |
| | | | 180 | | | | | 185 | | | | | 190 | | |

| Tyr | Asp | Tyr | Leu | Met | Tyr | Ala | Asp | Ile | Asp | Tyr | Asp | His | Pro | Asp | Val |
| | | | 195 | | | | | 200 | | | | | 205 | | |

| Ala | Ala | Glu | Ile | Lys | Arg | Trp | Gly | Thr | Trp | Tyr | Ala | Asn | Glu | Leu | Gln |
| 210 | | | | | 215 | | | | | 220 | | | | | |

| Leu | Asp | Gly | Phe | Arg | Leu | Asp | Ala | Val | Lys | His | Ile | Lys | Phe | Ser | Phe |
| 225 | | | | | 230 | | | | | 235 | | | | | 240 |

| Leu | Arg | Asp | Trp | Val | Asn | His | Val | Arg | Glu | Lys | Thr | Gly | Lys | Glu | Met |
| | | | | 245 | | | | | 250 | | | | | 255 | |

| Phe | Thr | Val | Ala | Glu | Tyr | Trp | Gln | Asn | Asp | Leu | Gly | Ala | Leu | Glu | Asn |
| | | | 260 | | | | | 265 | | | | | 270 | | |

| Tyr | Leu | Asn | Lys | Thr | Asn | Phe | Asn | His | Ser | Val | Phe | Asp | Val | Pro | Leu |
| | | | 275 | | | | | 280 | | | | | 285 | | |

| His | Tyr | Gln | Phe | His | Ala | Ala | Ser | Thr | Gln | Gly | Gly | Gly | Tyr | Asp | Met |
| | | | 290 | | | | | 295 | | | | | 300 | | |

| Arg | Lys | Leu | Leu | Asn | Gly | Thr | Val | Val | Ser | Lys | His | Pro | Leu | Lys | Ser |
| 305 | | | | | 310 | | | | | 315 | | | | | 320 |

| Val | Thr | Phe | Val | Asp | Asn | His | Asp | Thr | Gln | Pro | Gly | Gln | Ser | Leu | Glu |
| | | | | 325 | | | | | 330 | | | | | 335 | |

| Ser | Thr | Val | Gln | Thr | Trp | Phe | Lys | Pro | Leu | Ala | Tyr | Ala | Phe | Ile | Leu |
| | | | 340 | | | | | 345 | | | | | 350 | | |

| Thr | Arg | Glu | Ser | Gly | Tyr | Pro | Gln | Val | Phe | Tyr | Gly | Asp | Met | Tyr | Gly |
| | | 355 | | | | | 360 | | | | | 365 | | | |

| Thr | Lys | Gly | Asp | Ser | Gln | Arg | Glu | Ile | Pro | Ala | Leu | Lys | His | Lys | Ile |
| | 370 | | | | | 375 | | | | | 380 | | | | |

| Glu | Pro | Ile | Leu | Lys | Ala | Arg | Lys | Gln | Tyr | Ala | Tyr | Gly | Ala | Gln | His |
| 385 | | | | | 390 | | | | | 395 | | | | | 400 |

| Asp | Tyr | Phe | Asp | His | His | Asp | Ile | Val | Gly | Trp | Thr | Arg | Glu | Gly | Asp |
| | | | | 405 | | | | | 410 | | | | | 415 | |

```
Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
            450                 455                 460

Glu Gly Trp Gly Glu Phe His Val Asn Gly Ser Val Ser Ile Tyr
465             470                 475                 480

Val Gln Arg

<210> SEQ ID NO 5
<211> LENGTH: 480
<212> TYPE: PRT
<213> ORGANISM: Bacillus amyloliquefaciens

<400> SEQUENCE: 5

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65              70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
            115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300
```

```
Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
        340                 345                 350

Thr Arg Glu Ser Gly Tyr Pro Gln Val Phe Tyr Gly Asp Met Tyr Gly
    355                 360                 365

Thr Lys Gly Thr Ser Pro Lys Glu Ile Pro Ser Leu Lys Asp Asn Ile
370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
            405                 410                 415

Ser Ser Ala Ala Lys Ser Gly Leu Ala Ala Leu Ile Thr Asp Gly Pro
        420                 425                 430

Gly Gly Ser Lys Arg Met Tyr Ala Gly Leu Lys Asn Ala Gly Glu Thr
    435                 440                 445

Trp Tyr Asp Ile Thr Gly Asn Arg Ser Asp Thr Val Lys Ile Gly Ser
450                 455                 460

Asp Gly Trp Gly Glu Phe His Val Asn Asp Gly Ser Val Ser Ile Tyr
465                 470                 475                 480

<210> SEQ ID NO 6
<211> LENGTH: 485
<212> TYPE: PRT
<213> ORGANISM: Bacillus

<400> SEQUENCE: 6

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
        100                 105                 110

Ala Thr Glu Met Val Arg Ala Val Glu Val Asn Pro Asn Asn Arg Asn
    115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
            165                 170                 175

Ile Tyr Lys Phe Arg Gly His Gly Lys Ala Trp Asp Trp Glu Val Asp
        180                 185                 190

Thr Glu Asn Gly Asn Tyr Asp Tyr Leu Met Tyr Ala Asp Ile Asp Met
    195                 200                 205
```

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 7
<211> LENGTH: 485
<212> TYPE: PRT
<213> ORGANISM: Bacillus

<400> SEQUENCE: 7

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

```
Ile Gln Val Tyr Gly Asp Val Val Met Asn His Lys Gly Gly Ala Asp
                100                 105                 110

Gly Thr Glu Ile Val Asn Ala Val Glu Val Asn Arg Ser Asn Arg Asn
            115                 120                 125

Gln Glu Thr Ser Gly Glu Tyr Ala Ile Glu Ala Trp Thr Lys Phe Asp
        130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
            245                 250                 255

Thr Gly Lys Pro Met Phe Ala Val Ala Glu Phe Trp Lys Asn Asp Leu
        260                 265                 270

Gly Ala Ile Glu Asn Tyr Leu Asn Lys Thr Ser Trp Asn His Ser Val
            275                 280                 285

Phe Asp Val Pro Leu His Tyr Asn Leu Tyr Asn Ala Ser Asn Ser Gly
290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
            405                 410                 415

Gly Asn Ser Ser His Pro Asn Ser Gly Leu Ala Thr Ile Met Ser Asp
        420                 425                 430

Gly Pro Gly Gly Asn Lys Trp Met Tyr Val Gly Lys Asn Lys Ala Gly
    435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
                485

<210> SEQ ID NO 8
<211> LENGTH: 485
<212> TYPE: PRT
<213> ORGANISM: Bacillus
```

-continued

```
<400> SEQUENCE: 8

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415
```

```
Gly Asn Thr Thr His Pro Asn Ser Gly Leu Ala Thr Ile Met Ser Asp
                420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 9
<211> LENGTH: 1455
<212> TYPE: DNA
<213> ORGANISM: Bacillus

<400> SEQUENCE: 9
catcataatg gaacaaatgg tactatgatg caatatttcg aatggtattt gccaaatgac      60
gggaatcatt ggaacaggtt gagggatgac gcagctaact taaagagtaa agggataaca     120
gctgtatgga tcccacctgc atggaagggg acttcccaga tgatgtaggt tatggagcc     180 tatgatttat atgatcttgg agagtttaac cagaagggga cggttcgtac aaaatatgga     240
acacgcaacc agctacaggc tgcggtgacc tctttaaaaa ataacggcat tcaggtatat     300
ggtgatgtcg tcatgaatca taaaggtgga gcagatggta cggaaattgt aaatgcggta     360
gaagtgaatc ggagcaaccg aaaccaggaa acctcaggag agtatgcaat agaagcgtgg     420
acaaagtttg atttttcctgg aagaggaaat aaccattcca gctttaagtg gcgctggtat     480
cattttgatg ggacagattg ggatcagtca cgccagcttc aaaacaaaat atataaattc     540
aggggaacag gcaaggcctg ggactgggaa gtcgatacag agaatggcaa ctatgactat     600
cttatgtatg cagacgtgga tatggatcac ccagaagtaa tacatgaact tagaaactgg     660
ggagtgtggt atacgaatac actgaacctt gatggattta gaatagatgc agtgaaacat     720
ataaaatata gctttacgag agattggctt acacatgtgc gtaacaccac aggtaaacca     780
atgtttgcag tggctgagtt ttggaaaaat gaccttggtg caattgaaaa ctatttgaat     840
aaaacaagtt ggaatcactc ggtgtttgat gttcctctcc actataattt gtacaatgca     900
tctaatagcg gtggttatta tgatatgaga aatattttaa atggttctgt ggtgcaaaaa     960
catccaacac atgccgttac ttttgttgat aaccatgatt ctcagcccgg ggaagcattg    1020
gaatcctttg ttcaacaatg gtttaaacca cttgcatatg cattggttct gacaagggaa    1080
caaggttatc cttccgtatt ttatgggat tactacggta tcccaaccca tggtgttccg    1140
gctatgaaat ctaaaataga ccctcttctg caggcacgtc aaacttttgc ctatggtacg    1200
cagcatgatt acttttgatca tcatgatatt atcggttgga caagagaggg aaatagctcc    1260
catccaaatt caggccttgc caccattatg tcagatggtc caggtggtaa caaatggatg    1320
tatgtgggga aaaataaagc gggacaagtt tggagagata ttaccggaaa taggacaggc    1380
accgtcacaa ttaatgcaga cggatggggt aatttctctg ttaatggagg gtccgtttcg    1440
gtttgggtga agcaa                                                     1455

<210> SEQ ID NO 10
<211> LENGTH: 1455
<212> TYPE: DNA
<213> ORGANISM: Bacillus
```

<400> SEQUENCE: 10

```
catcataatg ggacaaatgg gacgatgatg caatactttg aatggcactt gcctaatgat      60
gggaatcact ggaatagatt aagagatgat gctagtaatc taagaaatag aggtataacc     120
gctatttgga ttccgcctgc ctggaaaggg acttcgcaaa atgatgtggg gtatggagcc     180
tatgatcttt atgatttagg ggaatttaat caaaagggga cggttcgtac taagtatggg     240
acacgtagtc aattggagtc tgccatccat gctttaaaga ataatggcgt tcaagtttat     300
ggggatgtag tgatgaacca taaggagga gctgatgcta cagaaaacgt tcttgctgtc      360
gaggtgaatc caaataaccg gaatcaagaa atatctgggg actacacaat tgaggcttgg     420
actaagtttg attttccagg gagggtaat acatactcag actttaaatg gcgttggtat      480
catttcgatg tgtagattg ggatcaatca cgacaattcc aaaatcgtat ctacaaattc      540
cgaggtgatg gtaaggcatg ggattgggaa gtagattcgg aaaatggaaa ttatgattat     600
ttaatgtatg cagatgtaga tatggatcat ccggaggtag taaatgagct tagaagatgg     660
ggagaatggt atacaaatac attaaatctt gatggattta ggatcgatgc ggtgaagcat     720
attaaatata gctttacacg tgattggttg acccatgtaa aaacgcaac gggaaaagaa      780
atgtttgctg ttgctgaatt ttggaaaaat gatttaggtg ccttggagaa ctatttaaat     840
aaaacaaact ggaatcattc tgtctttgat gtccccttc attataatct ttataacgcg      900
tcaaatagtg gaggcaacta tgacatggca aaacttctta atggaacggt tgttcaaaag     960
catccaatgc atgccgtaac ttttgtggat aatcacgatt ctcaacctgg ggaatcatta    1020
gaatcatttg tacaagaatg gtttaagcca cttgcttatg cgcttatttt aacaagagaa    1080
caaggctatc cctctgtctt ctatggtgac tactatggaa ttccaacaca tagtgtccca    1140
gcaatgaaag ccaagattga tccaatctta gaggcgcgtc aaaattttgc atatggaaca    1200
caacatgatt attttgacca tcataatata atcggatgga cacgtgaagg aaataccacg    1260
catcccaatt caggacttgc gactatcatg tcggatgggc caggggaga gaaatggatg     1320
tacgtagggc aaaataaagc aggtcaagtt tggcatgaca taactggaaa taaaccagga    1380
acagttacga tcaatgcaga tggatgggct aattttcag taaatggagg atctgtttcc    1440
atttgggtga aacga                                                    1455
```

<210> SEQ ID NO 11
<211> LENGTH: 1548
<212> TYPE: DNA
<213> ORGANISM: Bacillus stearothermophilus

<400> SEQUENCE: 11

```
gccgcaccgt ttaacggcac catgatgcag tattttgaat ggtacttgcc ggatgatggc     60
acgttatgga ccaaagtggc caatgaagcc aacaacttat ccagccttgg catcaccgct    120
ctttggctgc cgcccgctta caaaggaaca agccgcagcg acgtagggta cggagtatac    180
gacttgtatg acctcggcga attcaatcaa aaagggaccg tccgcacaaa atacggaaca    240
aaagctcaat atcttcaagc cattcaagcc gcccacgccg ctggaatgca agtgtacgcc    300
gatgtcgtgt tcgaccataa aggcggcgct gacggcacgg aatgggtgga cgccgtcgaa    360
gtcaatccgt ccgaccgcaa ccaagaaatc tcgggcaccc atcaaatcca agcatggacg    420
aaatttgatt ttcccgggcg gggcaacacc tactccagct ttaagtggcg ctggtaccat    480
tttgacggcg ttgattggga cgaaagccga aaattgagcc gcatttacaa attccgcggc    540
atcggcaaag cgtgggattg ggaagtagac acggaaaacg gaaactatga ctacttaatg    600
```

-continued

| | |
|---|---|
| tatgccgacc ttgatatgga tcatcccgaa gtcgtgaccg agctgaaaaa ctgggggaaa | 660 |
| tggtatgtca acacaacgaa cattgatggg ttccggcttg atgccgtcaa gcatattaag | 720 |
| ttcagtttt ttcctgattg gttgtcgtat gtgcgttctc agactggcaa gccgctattt | 780 |
| accgtcgggg aatattggag ctatgacatc aacaagttgc acaattacat tacgaaaaca | 840 |
| gacggaacga tgtctttgtt tgatgccccg ttacacaaca aattttatac cgcttccaaa | 900 |
| tcagggggcg catttgatat gcgcacgtta atgaccaata ctctcatgaa agatcaaccg | 960 |
| acattggccg tcaccttcgt tgataatcat gacaccgaac ccggccaagc gctgcagtca | 1020 |
| tgggtcgacc catggttcaa accgttggct tacgcctta ttctaactcg gcaggaagga | 1080 |
| tacccgtgcg tcttttatgg tgactattat ggcattccac aatataacat tccttcgctg | 1140 |
| aaaagcaaaa tcgatccgct cctcatcgcg cgcaggatt atgcttacgg aacgcaacat | 1200 |
| gattatcttg atcactccga catcatcggg tggacaaggg aagggggcac tgaaaaacca | 1260 |
| ggatccggac tggccgcact gatcaccgat gggccgggag aagcaaatg gatgtacgtt | 1320 |
| ggcaaacaac acgctggaaa agtgttctat gaccttaccg gcaaccggag tgacaccgtc | 1380 |
| accatcaaca gtgatggatg gggggaattc aaagtcaatg gcggttcggt ttcggtttgg | 1440 |
| gttcctagaa aaacgaccgt ttctaccatc gctcggccga tcacaacccg accgtggact | 1500 |
| ggtgaattcg tccgttggac cgaaccacgg ttggtggcat ggccttga | 1548 |

<210> SEQ ID NO 12
<211> LENGTH: 1920
<212> TYPE: DNA
<213> ORGANISM: Bacillus licheniformis
<220> FEATURE:
<221> NAME/KEY: misc_feature
<222> LOCATION: (421)..(1872)
<223> OTHER INFORMATION: CDS

<400> SEQUENCE: 12

| | |
|---|---|
| cggaagattg gaagtacaaa aataagcaaa agattgtcaa tcatgtcatg agccatgcgg | 60 |
| gagacggaaa aatcgtctta atgcacgata tttatgcaac gttcgcagat gctgctgaag | 120 |
| agattattaa aaagctgaaa gcaaaaggct atcaattggt aactgtatct cagcttgaag | 180 |
| aagtgaagaa gcagagaggc tattgaataa atgagtagaa gcgccatatc ggcgcttttc | 240 |
| ttttggaaga aaatataggg aaaatggtac ttgttaaaaa ttcggaatat ttatacaaca | 300 |
| tcatatgttt cacattgaaa ggggaggaga atcatgaaac aacaaaaacg gctttacgcc | 360 |
| cgattgctga cgctgttatt tgcgctcatc ttccttgctgc ctcattctgc agcagcggcg | 420 |
| gcaaatctta atgggacgct gatgcagtat tttgaatggt acatgcccaa tgacggccaa | 480 |
| cattggaggc gtttgcaaaa cgactcggca tatttggctg aacacggtat tactgccgtc | 540 |
| tggattcccc cggcatataa gggaacgagc caagcggatg tgggctacgg tgcttacgac | 600 |
| ctttatgatt tagggagtt tcatcaaaaa gggacggttc ggacaaagta cggcacaaaa | 660 |
| ggagagctgc aatctgcgat caaaagtctt cattcccgcg acattaacgt ttacggggat | 720 |
| gtggtcatca accacaaagg cggcgctgat gcgaccgaag atgtaaccgc ggttgaagtc | 780 |
| gatcccgctg accgcaaccg cgtaatttca ggagaacacc taattaaagc ctggacacat | 840 |
| tttcattttc cggggcgcgg cagcacatac agcgatttta aatggcattg gtaccatttt | 900 |
| gacggaaccg attgggacga gtcccgaaag ctgaaccgca tctataagtt caaggaaag | 960 |
| gcttgggatt gggaagtttc caatgaaaac ggcaactatg attatttgat gtatgccgac | 1020 |
| atcgattatg accatcctga tgtcgcagca gaaattaaga gatggggcac ttggtatgcc | 1080 |

-continued

```
aatgaactgc aattggacgg tttccgtctt gatgctgtca aacacattaa attttctttt    1140
ttgcgggatt gggttaatca tgtcagggaa aaacgggga aggaaatgtt tacggtagct    1200
gaatattggc agaatgactt gggcgcgctg gaaaactatt tgaacaaaac aaatttttaat    1260
cattcagtgt ttgacgtgcc gcttcattat cagttccatg ctgcatcgac acagggaggc    1320
ggctatgata tgaggaaatt gctgaacggt acggtcgttt ccaagcatcc gttgaaatcg    1380
gttacatttg tcgataacca tgatacacag ccggggcaat cgcttgagtc gactgtccaa    1440
acatggttta agccgcttgc ttacgctttt attctcacaa gggaatctgg ataccctcag    1500
gttttctacg gggatatgta cgggacgaaa ggagactccc agcgcgaaat tcctgccttg    1560
aaacacaaaa ttgaaccgat cttaaaagcg agaaaacagt atgcgtacgg agcacagcat    1620
gattatttcg accaccatga cattgtcggc tggacaaggg aaggcgacag ctcggttgca    1680
aattcaggtt tggcggcatt aataacagac ggacccggtg gggcaaagcg aatgtatgtc    1740
ggccggcaaa acgccggtga gacatggcat gacattaccg gaaaccgttc ggagccggtt    1800
gtcatcaatt cggaaggctg gggagagttt cacgtaaacg gcgggtcggt ttcaatttat    1860
gttcaaagat agaagagcag agaggacgga tttcctgaag gaaatccgtt ttttttatttt    1920
```

<210> SEQ ID NO 13
<211> LENGTH: 1455
<212> TYPE: DNA
<213> ORGANISM: Bacillus

<400> SEQUENCE: 13

```
catcataatg gaacaaatgg tactatgatg caatatttcg aatggtattt gccaaatgac      60
gggaatcatt ggaacaggtt gagggatgac gcagctaact taaagagtaa agggataaca     120
gctgtatgga tcccacctgc atggaagggg acttcccaga tgatgtagg ttatggagcc     180
tatgatttat atgatcttgg agagtttaac cagaagggga cggttcgtac aaaatatgga     240
acacgcaacc agctacaggc tgcggtgacc tctttaaaaa ataacggcat tcaggtatat     300
ggtgatgtcg tcatgaatca taaaggtgga gcagatggta cggaaattgt aaatgcggta     360
gaagtgaatc ggagcaaccg aaaccaggaa acctcaggag agtatgcaat agaagcgtgg     420
acaaagtttg attttcctgg aagaggaaat aaccattcca gctttaagtg gcgctggtat     480
cattttgatg ggacagattg ggatcagtca cgccagcttc aaaacaaaat atataaattc     540
aggggaacag gcaaggcctg ggactgggaa gtcgatacag agaatggcaa ctatgactat     600
cttatgtatg cagacgtgga tatggatcac ccagaagtaa tacatgaact tagaaactgg     660
ggagtgtggt atacgaatac actgaacctt gatggattta aatagatgc agtgaaacat     720
ataaaatata gctttacgag agattggctt acacatgtgc gtaacaccac aggtaaacca     780
atgtttgcag tggctgagtt ttggaaaaat gaccttggtg caattgaaaa ctatttgaat     840
aaaacaagtt ggaatcactc ggtgtttgat gttcctctcc actataattt gtacaatgca     900
tctaatagcg gtggttatta tgatatgaga aatatttaa atggttctgt ggtgcaaaaa     960
catccaacac atgccgttac ttttgttgat aaccatgatt ctcagcccgg ggaagcattg    1020
gaatcctttg ttcaacaatg gttaaaccca cttgcatatg cattggttct gacaagggaa    1080
caaggttatc cttccgtatt ttatgggat tactacggta tcccaaccca tggtgttccg    1140
gctatgaaat ctaaaataga ccctcttctg caggcacgtc aaacttttgc ctatggtacg    1200
cagcatgatt actttgatca tcatgatatt atcggttgga caagagaggg aaatagctcc    1260
```

-continued

```
catccaaatt caggccttgc caccattatg tcagatggtc caggtggtaa caaatggatg    1320
tatgtgggga aaaataaagc gggacaagtt tggagagata ttaccggaaa taggacaggc    1380
accgtcacaa ttaatgcaga cggatggggt aatttctctg ttaatggagg gtccgtttcg    1440
gtttgggtga agcaa                                                     1455

<210> SEQ ID NO 14
<211> LENGTH: 1455
<212> TYPE: DNA
<213> ORGANISM: Bacillus

<400> SEQUENCE: 14
catcataatg ggacaaatgg gacgatgatg caatactttg aatggcactt gcctaatgat     60
gggaatcact ggaatagatt aagagatgat gctagtaatc taagaaatag aggtataacc    120
gctatttgga ttccgcctgc ctggaaaggg acttcgcaaa atgatgtggg gtatggagcc    180
tatgatcttt atgatttagg ggaatttaat caaaagggga cggttcgtac taagtatggg    240
acacgtagtc aattggagtc tgccatccat gctttaaaga ataatggcgt tcaagtttat    300
ggggatgtag tgatgaacca taaggagga gctgatgcta cagaaaacgt tcttgctgtc    360
gaggtgaatc caaataaccg gaatcaagaa atatctgggg actacacaat tgaggcttgg    420
actaagtttg attttccagg gaggggtaat acatactcag actttaaatg cgttggtat    480 catttcgatg tgtagattg ggatcaatca cgacaattcc aaaatcgtat ctacaaattc     540
cgaggtgatg gtaaggcatg ggattgggaa gtagattcgg aaaatggaaa ttatgattat    600
ttaatgtatg cagatgtaga tatggatcat ccggaggtag taaatgagct tagaagatgg    660
ggagaatggt atacaaatac attaaatctt gatggattta ggatcgatgc ggtgaagcat    720
attaaatata gctttacacg tgattggttg acccatgtaa gaaacgcaac gggaaaagaa    780
atgtttgctg ttgctgaatt ttggaaaaat gatttaggtg ccttggagaa ctatttaaat    840
aaaacaaact ggaatcattc tgtctttgat gtccccttc attataatct ttataacgcg    900
tcaaatagtg gaggcaacta tgacatggca aaacttctta atggaacggt tgttcaaaag    960
catccaatgc atgccgtaac ttttgtggat aatcacgatt ctcaacctgg ggaatcatta   1020
gaatcatttg tacaagaatg gtttaagcca cttgcttatg cgcttatttt aacaagagaa   1080
caaggctatc cctctgtctt ctatggtgac tactatggaa ttccaacaca tagtgtccca   1140
gcaatgaaag ccaagattga tccaatcta gaggcgcgtc aaaattttgc atatggaaca   1200
caacatgatt attttgacca tcataatata atcggatgga cacgtgaagg aaataccacg   1260
catcccaatt caggacttgc gactatcatg tcggatgggc caggggagga gaaatggatg   1320
tacgtagggc aaaataaagc aggtcaagtt tggcatgaca taactggaaa taaaccagga   1380
acagttacga tcaatgcaga tggatgggct aattttttcag taaatggagg atctgttttcc   1440 atttgggtga aacga                                                    1455

<210> SEQ ID NO 15
<211> LENGTH: 74
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (21)..(62)
<223> OTHER INFORMATION: N is a, c, t or g
```

```
<400> SEQUENCE: 15
gcgttttgcc ggccgacata nnnnnnnnnn nnnnnnnnnn nnnnnnnnnn nnnnnnnnnn    60
nncaaacctg aatt                                                     74

<210> SEQ ID NO 16
<211> LENGTH: 122
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (63)..(104)
<223> OTHER INFORMATION: N is a, c, t or g

<400> SEQUENCE: 16
gcgttttgcc ggccgacata cattcgcttt gccccaccgg gtccgtctgt tattaatgcc    60
gcnnnnnnnn nnnnnnnnnn nnnnnnnnnn nnnnnnnnnn nnnngccgac aatgtcatgg   120
tg                                                                 122

<210> SEQ ID NO 17
<211> LENGTH: 78
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (19)..(60)
<223> OTHER INFORMATION: n is a, c, t or g

<400> SEQUENCE: 17
gtcgccttcc cttgtccann nnnnnnnnnn nnnnnnnnnn nnnnnnnnnn nnnnnnnnnn    60
gtacgcatac tgttttct                                                 78

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
tggacaaggg aaggcgacag                                               20

<210> SEQ ID NO 19
<211> LENGTH: 81
<212> TYPE: DNA
<213> ORGANISM: Artificial sequence
<220> FEATURE:
<223> OTHER INFORMATION: Primer RSERV
<220> FEATURE:
<221> NAME/KEY: misc_feature
<222> LOCATION: (19)..(60)
<223> OTHER INFORMATION: N is a, c, t or g

<400> SEQUENCE: 19
taagatcggt tcaattttnn nnnnnnnnnn nnnnnnnnnn nnnnnnnnnn nnnnnnnnnn    60
cccgtacata tccccgtaga a                                             81

<210> SEQ ID NO 20
<211> LENGTH: 18
<212> TYPE: DNA
<213> ORGANISM: Artificial sequence
```

-continued

```
<220> FEATURE:
<223> OTHER INFORMATION: Primer

<400> SEQUENCE: 20
aaaattgaac cgatctta                                                        18

<210> SEQ ID NO 21
<211> LENGTH: 107
<212> TYPE: DNA
<213> ORGANISM: Artificial sequence
<220> FEATURE:
<223> OTHER INFORMATION: Primer FSERVII
<220> FEATURE:
<221> NAME/KEY: misc_feature
<222> LOCATION: (54)..(95)
<223> OTHER INFORMATION: N is a, c, t or g

<400> SEQUENCE: 21
ttccatgctg catcgacaca gggaggcggc tatgatatga ggaaattgct gaannnnnnn          60
nnnnnnnnnn nnnnnnnnnn nnnnnnnnnn nnnnntgtcg ataacca                       107

<210> SEQ ID NO 22
<211> LENGTH: 18
<212> TYPE: DNA
<213> ORGANISM: Artificial sequence
<220> FEATURE:
<223> OTHER INFORMATION: Primer

<400> SEQUENCE: 22
tgtcgatgca gcatggaa                                                        18

<210> SEQ ID NO 23
<211> LENGTH: 80
<212> TYPE: DNA
<213> ORGANISM: Artificial sequence
<220> FEATURE:
<223> OTHER INFORMATION: Primer FSERIX
<220> FEATURE:
<221> NAME/KEY: misc_feature
<222> LOCATION: (21)..(62)
<223> OTHER INFORMATION: N is a, c, t or g

<400> SEQUENCE: 23
gtccaaacat ggtttaagcc nnnnnnnnnn nnnnnnnnnn nnnnnnnnnn nnnnnnnnnn          60
nntcaggttt tctacgggga                                                      80

<210> SEQ ID NO 24
<211> LENGTH: 20
<212> TYPE: DNA
<213> ORGANISM: Artificial sequence
<220> FEATURE:
<223> OTHER INFORMATION: Primer

<400> SEQUENCE: 24
ggcttaaacc atgtttggac                                                      20

<210> SEQ ID NO 25
<211> LENGTH: 24
<212> TYPE: DNA
<213> ORGANISM: Artificial sequence
<220> FEATURE:
<223> OTHER INFORMATION: Primer

<400> SEQUENCE: 25
cgattgctga cgctgttatt tgcg                                                 24
```

```
<210> SEQ ID NO 26
<211> LENGTH: 25
<212> TYPE: DNA
<213> ORGANISM: Artificial sequence
<220> FEATURE:
<223> OTHER INFORMATION: Primer

<400> SEQUENCE: 26
ctatctttga acataaattg aaacc                                            25

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
gacctgcagt caggcaacta                                                  20

<210> SEQ ID NO 28
<211> LENGTH: 20
<212> TYPE: DNA
<213> ORGANISM: Artificial sequence
<220> FEATURE:
<223> OTHER INFORMATION: Primer

<400> SEQUENCE: 28
tagagtcgac ctgcaggcat                                                  20

<210> SEQ ID NO 29
<211> LENGTH: 20
<212> TYPE: DNA
<213> ORGANISM: Artificial sequence
<220> FEATURE:
<223> OTHER INFORMATION: Forward Primer2

<400> SEQUENCE: 29
gacctgcagt caggcaacta                                                  20

<210> SEQ ID NO 30
<211> LENGTH: 20
<212> TYPE: DNA
<213> ORGANISM: Artificial sequence
<220> FEATURE:
<223> OTHER INFORMATION: Primer

<400> SEQUENCE: 30
tagagtcgac ctgcaggcat                                                  20

<210> SEQ ID NO 31
<211> LENGTH: 2084
<212> TYPE: DNA
<213> ORGANISM: Bacillus amyloliquefaciens
<220> FEATURE:
<221> NAME/KEY: misc_feature
<222> LOCATION: (343)..(1794)
<223> OTHER INFORMATION: CDS

<400> SEQUENCE: 31
gccccgcaca tacgaaaaga ctggctgaaa acattgagcc tttgatgact gatgatttgg      60
ctgaagaagt ggatcgattg tttgagaaaa gaagaagacc ataaaaatac cttgtctgtc     120
atcagacagg gtattttta tgctgtccag actgtccgct gtgtaaaaat aaggaataaa     180 gggggggttgt tattatttta ctgatatgta aaatataatt tgtataagaa aatgagaggg     240
agaggaaaca tgattcaaaa acgaaagcgg acagtttcgt tcagacttgt gcttatgtgc     300
```

```
acgctgttat tgtcagtttt gccgattaca aaaacatcag ccgtaaatgg cacgctgatg    360
cagtattttg aatggtatac gccgaacgac ggccagcatt ggaaacgatt gcagaatgat    420
gcggaacatt tatcggatat cggaatcact gccgtctgga ttcctcccgc atacaaagga    480
ttgagccaat ccgataacgg atacggacct tatgatttgt atgatttagg agaattccag    540
caaaaggga cggtcagaac gaaatacggc acaaaatcag agcttcaaga tgcgatcggc    600
tcactgcatt cccggaacgt ccaagtatac ggagatgtgg ttttgaatca taaggctggt    660
gctgatgcaa cagaagatgt aactgccgtc gaagtcaatc cggccaatag aaatcaggaa    720
acttcggagg aatatcaaat caaagcgtgg acggattttc gttttccggg ccgtggaaac    780
acgtacagtg attttaaatg gcattggtat catttcgacg gagcggactg ggatgaatcc    840
cggaagatca gccgcatctt taagtttcgt ggggaaggaa aagcgtggga ttgggaagta    900
tcaagtgaaa acggcaacta tgactattta atgtatgctg atgttgacta cgaccaccct    960
gatgtcgtgg cagagacaaa aaaatggggt atctggtatg cgaatgaact gtcattagac   1020
ggcttccgta ttgatgccgc caaacatatt aaattttcat ttctgcgtga ttgggttcag   1080
gcggtcagac aggcgacggg aaaagaaatg tttacggttg cggagtattg cagaataat   1140
gccgggaaac tcgaaaacta cttgaataaa acaagcttta atcaatccgt gtttgatgtt   1200
ccgcttcatt tcaatttaca ggcggcttcc tcacaaggag gcggatatga tatgaggcgt   1260
ttgctggacg gtaccgttgt gtccaggcat ccggaaaagg cggttacatt tgttgaaaat   1320
catgacacac agccgggaca gtcattggaa tcgacagtcc aaacttggtt taaaccgctt   1380
gcatacgcct ttatttgac aagagaatcc ggttatcctc aggtgttcta tggggatatg   1440
tacgggacaa aagggacatc gccaaaggaa attccctcac tgaaagataa tatagagccg   1500
attttaaaag cgcgtaagga gtacgcatac gggccccagc acgattatat tgaccacccg   1560
gatgtgatcg gatggacgag ggaaggtgac agctccgccg ccaaatcagg tttggccgct   1620
ttaatcacgg acgacccgg cggatcaaag cggatgtatg ccggcctgaa aaatgccggc   1680
gagacatggt atgacataac gggcaaccgt tcagatactg taaaaatcgg atctgacggc   1740
tggggagagt ttcatgtaaa cgatgggtcc gtctccattt atgttcagaa ataaggtaat   1800
aaaaaaacac ctccaagctg agtgcgggta tcagcttgga ggtgcgttta ttttttcagc   1860
cgtatgacaa ggtcggcatc aggtgtgaca aatacggtat gctggctgtc ataggtgaca   1920
aatccgggtt ttgcgccgtt tggcttttc acatgtctga ttttttgtata atcaacaggc   1980
acggagccga aatctttcgc cttggaaaaa taagcggcga tcgtagctgc ttccaatatg   2040
gattgttcat cgggatcgct gcttttaatc acaacgtggg atcc                   2084
```

<210> SEQ ID NO 32
<211> LENGTH: 400
<212> TYPE: PRT
<213> ORGANISM: Bacillus

<400> SEQUENCE: 32

```
Asn Gly Thr Asn Gly Thr Met Met Gln Tyr Phe Glu Trp Tyr Leu Pro
1               5                   10                  15

Asn Asp Gly Asn His Trp Asn Arg Leu Arg Ser Asp Ala Ser Asn Leu
            20                  25                  30

Lys Asp Lys Gly Ile Ser Ala Val Trp Ile Pro Pro Ala Trp Lys Gly
        35                  40                  45

Ala Ser Gln Asn Asp Val Gly Tyr Gly Ala Tyr Asp Leu Tyr Asp Leu
    50                  55                  60
```

```
Gly Glu Phe Asn Gln Lys Gly Thr Ile Arg Thr Lys Tyr Gly Thr Arg
65                  70                  75                  80

Asn Gln Leu Gln Ala Ala Val Asn Ala Leu Lys Ser Asn Gly Ile Gln
                85                  90                  95

Val Tyr Gly Asp Val Val Met Asn His Lys Gly Gly Ala Asp Ala Thr
            100                 105                 110

Glu Met Val Arg Ala Val Glu Val Asn Pro Asn Asn Arg Asn Gln Glu
        115                 120                 125

Val Ser Gly Glu Tyr Thr Ile Glu Ala Trp Thr Lys Phe Asp Phe Pro
130                 135                 140

Gly Arg Gly Asn Thr His Ser Asn Phe Lys Trp Arg Trp Tyr His Phe
145                 150                 155                 160

Asp Gly Val Asp Trp Asp Gln Ser Arg Lys Leu Asn Asn Arg Ile Tyr
                165                 170                 175

Lys Phe Arg Gly Asp Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ser Ile His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285

Val Pro Leu His Tyr Asn Phe Tyr Asn Ala Ser Lys Ser Gly Gly Asn
    290                 295                 300

Tyr Asp Met Arg Gln Ile Phe Asn Gly Thr Val Val Gln Arg His Pro
305                 310                 315                 320

Met His Ala Val Thr Phe Val Asp Asn His Asp Ser Gln Pro Glu Glu
                325                 330                 335

Ala Leu Glu Ser Phe Val Glu Val Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Arg Gln Asn
385                 390                 395                 400
```

ALPHA-AMYLASE VARIANTS

CROSS-REFERENCE TO RELATED APPLICATIONS

This application is a divisional of U.S. application Ser. No. 13/038,991 filed on Mar. 2, 2011, now abandoned, which is a divisional of U.S. application Ser. No. 12/417,453 filed on Apr. 2, 2009, now abandoned, which is a divisional of U.S. application Ser. No. 11/039,565 filed Jan. 19, 2005, now U.S. Pat. No. 7,601,527, which is a continuation of U.S. application Ser. No. 09/441,313, filed Nov. 16, 1999, now U.S. Pat. No. 6,887,986, which is a continuation-in-part of U.S. application Ser. No. 09/193,068 filed on Nov. 16, 1998, now U.S. Pat. No. 6,197,565, the contents of which are fully incorporated herein by reference.

FIELD OF THE INVENTION

The present invention relates to novel variants of parent Termamyl-like alpha-amylases with altered properties relative of the parent alpha-amylase. Said properties include increased stability, e.g., at acidic pH, e.g., at low calcium concentrations and/or high temperatures. Such variants are suitable for a number of applications, in particular, industrial starch processing (e.g., starch liquefaction or saccharification).

BACKGROUND OF THE INVENTION

Alpha-Amylases (alpha-1,4-glucan-4-glucanohydrolases, EC 3.2.1.1) constitute a group of enzymes which catalyze hydrolysis of starch and other linear and branched 1,4-glucosidic oligo- and polysaccharides.

There is a very extensive body of patent and scientific literature relating to this industrially very important class of enzymes. A number of alpha-amylase such as Termamyl-like alpha-amylases variants are known from, e.g., WO 90/11352, WO 95/10603, WO 95/26397, WO 96/23873 and WO 96/23874.

WO 96/23874 provides the three-dimensional, X-ray crystal structural data for a Termamyl-like alpha-amylase which consists of the 300 N-terminal amino acid residues of the B. amyloliquefaciens alpha-amylase and amino acids 301-483 of the C-terminal end of the B. licheniformis alpha-amylase comprising the amino acid sequence (the latter being available commercially under the tradename Termamyl™), and which is thus closely related to the industrially important Bacillus alpha-amylases (which in the present context are embraced within the meaning of the term "Termamyl-like alpha-amylases", and which include, inter alia, the B. licheniformis, B. amyloliquefaciens and B. stearothermophilus alpha-amylases). WO 96/23874 further describes methodology for designing, on the basis of an analysis of the structure of a parent Termamyl-like alpha-amylase, variants of the parent Termamyl-like alpha-amylase which exhibit altered properties relative to the parent.

BRIEF DISCLOSURE OF THE INVENTION

The present invention relates to alpha-amylolytic variants (mutants) of a Termamyl-like alpha-amylase, in particular variants exhibiting increased stability at acidic pH at high temperatures (relative to the parent) which are advantageous in connection with, e.g., the industrial processing of starch (starch liquefaction, saccharification and the like) as described in U.S. Pat. No. 3,912,590 and EP patent publications Nos. 252730 and 063909.

Starch Conversion

A "traditional" starch conversion process degrading starch to lower molecular weight carbohydrate components such as sugars or fat replacers includes a debranching step.

"Starch to Sugar" Conversion

In the case of converting starch into a sugar the starch is depolymerized. A such depolymerization process consists of a pretreatment step and two or three consecutive process steps, viz. a liquefaction process, a saccharification process and dependent on the desired end product optionally an isomerization process.

Pre-Treatment of Native Starch

Native starch consists of microscopic granules which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typically industrial process, the starch has to be thinned or "liquefied" so that it can be handled. This reduction in viscosity is today mostly obtained by enzymatic degradation.

Liquefaction

During the liquefaction step, the long chained starch is degraded into branched and linear shorter units (maltodextrins) by an alpha-amylase (e.g., Termamyl™ SEQ ID NO: 4 herein). The liquefaction process is carried out at 105-110° C. for 5 to 10 minutes followed by 1-2 hours at 95° C. The pH lies between 5.5 and 6.2. In order to ensure an optimal enzyme stability under these conditions, 1 mM of calcium is added (40 ppm free calcium ions). After this treatment the liquefied starch will have a "dextrose equivalent" (DE) of 10-15.

Saccharification

After the liquefaction process the maltodextrins are converted into dextrose by addition of a glucoamylase (e.g., AMG™) and a debranching enzyme, such as an isoamylase (U.S. Pat. No. 4,335,208) or a pullulanase (e.g., Promozyme™) (U.S. Pat. No. 4,560,651). Before this step the pH is reduced to a value below 4.5, maintaining the high temperature (above 95° C.) to inactivate the liquefying alpha-amylase to reduce the formation of short oligosaccharide called "panose precursors" which cannot be hydrolyzed properly by the debranching enzyme.

The temperature is lowered to 60° C., and glucoamylase and debranching enzyme are added. The saccharification process proceeds for 24-72 hours.

Normally, when denaturing the alpha-amylase after the liquefaction step about 0.2-0.5% of the saccharification product is the branched trisaccharide $6^2$-alpha-glucosyl maltose (panose) which cannot be degraded by a pullulanase. If active amylase from the liquefaction step is present during saccharification (i.e., no denaturing), this level can be as high as 1-2%, which is highly undesirable as it lowers the saccharification yield significantly.

Isomerization

When the desired final sugar product is, e.g., high fructose syrup the dextrose syrup may be converted into fructose. After the saccharification process the pH is increased to a value in the range of 6-8, preferably pH 7.5, and the calcium is removed by ion exchange. The dextrose syrup is then converted into high fructose syrup using, e.g., an immmobilized glucoseisomerase (such as Sweetzyme™).

In the context of the invention the term "acidic pH" means a pH below 7.0, especially below the pH range in which industrial starch liquefaction processes are traditionally performed, as described above, which is between pH 5.5 and 6.2.

In the context of the present invention the term "low calcium concentration" means concentrations below the normal level used in traditional industrial starch liquefaction processes, such as between 0-40 ppm, preferably between 10-30 ppm, such as between 15-25 ppm calcium. Normal concentrations vary depending of the concentration of free $Ca^{2+}$ in the corn. Normally a dosage corresponding to 1 mM (40 ppm) is added which together with the level in corn gives between 40 and 60 ppm free $Ca^{2+}$.

In the context of the invention the term "high temperature" means temperatures between 95 and 160° C., especially the temperature range in which industrial starch liquefaction processes are normally performed, which is between 95 and 105° C.

The invention further relates to DNA constructs encoding variants of the invention, to methods for preparing variants of the invention, and to the use of variants of the invention, alone or in combination with other alpha-amylolytic enzymes, in various industrial processes, in particular starch liquefaction.

Nomenclature

In the present description and claims, the conventional one-letter and three-letter codes for amino acid residues are used. For ease of reference, alpha-amylase variants of the invention are described by use of the following nomenclature:

Original amino acid(s):position(s):substituted amino acid(s)

According to this nomenclature, for instance the substitution of alanine for asparagine in position 30 is shown as:

Asn30Ala or N30A a deletion of alanine in the same position is shown as:

Ala30* or A30* and insertion of an additional amino acid residue, such as lysine, is shown as:

Ala30AlaLys or A30AK

A deletion of a consecutive stretch of amino acid residues, such as amino acid residues 30-33, is indicated as (30-33)* or Δ(A30-N33).

Where a specific alpha-amylase contains a "deletion" in comparison with other alpha-amylases and an insertion is made in such a position this is indicated as:

*36Asp or *36D for insertion of an aspartic acid in position 36

Multiple mutations are separated by plus signs, i.e.:

Ala30Asp+Glu34Ser or A30D+E34S representing mutations in positions 30 and 34 substituting aspartic acid and serine for alanine and glutamic acid, respectively. Multiple mutations may also be separated as follows, i.e., meaning the same as the plus sign:

Ala30Asp/Glu34Ser or A30D/E34S

When one or more alternative amino acid residues may be inserted in a given position it is indicated as A30N,E or A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of: R,N,D,A,C,Q,E,G,H,I,L,K,M,F,P,S,T,W,Y,V.

BRIEF DESCRIPTION OF THE DRAWING

FIG. 1 is an alignment of the amino acid sequences of six parent Termamyl-like alpha-amylases in the context of the invention. The numbers on the Extreme left designate the respective amino acid sequences as follows:

Figure 2:
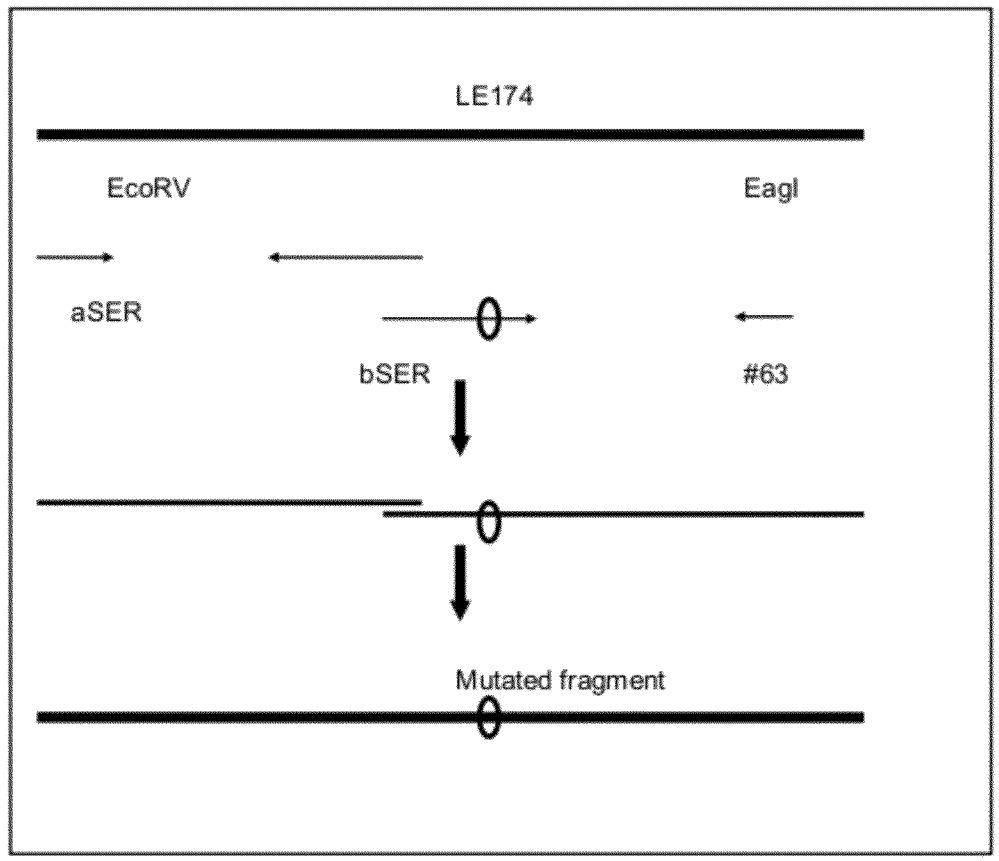

1: SEQ ID NO: 2,
2: amylase (SEQ ID NO: 32)
3: SEQ ID NO: 1,
4: SEQ ID NO: 5,
5: SEQ ID NO: 4,
6: SEQ ID NO: 3.

FIG. 2 shows the PCR strategy used in Example 1.

DETAILED DISCLOSURE OF THE INVENTION

The Termamyl-Like Alpha-Amylase

It is well known that a number of alpha-amylases produced by *Bacillus* spp. are highly homologous on the amino acid level. For instance, the *B. licheniformis* alpha-amylase comprising the amino acid sequence shown in SEQ ID NO: 4 (commercially available as Termamyl™) has been found to be about 89% homologous with the *B. amyloliquefaciens* alpha-amylase comprising the amino acid sequence shown in SEQ ID NO: 5 and about 79% homologous with the *B. stearothermophilus* alpha-amylase comprising the amino acid sequence shown in SEQ ID NO: 3. Further homologous alpha-amylases include an alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., 1988, *Biochemical and Biophysical Research Communications*, 151: 25-31.

Still further homologous alpha-amylases include the alpha-amylase produced by the *B. licheniformis* strain described in EP 0252666 (ATCC 27811), and the alpha-amylases identified in WO 91/00353 and WO 94/18314. Other commercial Termamyl-like *B. licheniformis* alpha-amylases are Optitherm™ and Takatherm™ (available from Solvay), Maxamyl™ (available from Gist-brocades/Genencor), Spezym AA™ and Spezyme Delta AA™ (available from Genencor), and Keistase™ (available from Daiwa).

Because of the substantial homology found between these alpha-amylases, they are considered to belong to the same class of alpha-amylases, namely the class of "Termamyl-like alpha-amylases".

Accordingly, in the present context, the term "Termamyl-like alpha-amylase" is intended to indicate an alpha-amylase which, at the amino acid level, exhibits a substantial homology to Termamyl™, i.e., the *B. licheniformis* alpha-amylase having the amino acid sequence shown in SEQ ID NO: 4 herein. In other words, a Termamyl-like alpha-amylase is an alpha-amylase which has the amino acid sequence shown in SEQ ID NOS: 1, 2, 3, 4, 5, 6, 7 or 8 herein, and the amino acid sequence shown in SEQ ID NO: 1 of WO 95/26397 (the same as the amino acid sequence shown as SEQ ID NO: 7 herein) or in SEQ ID NO: 2 of WO 95/26397 (the same as the amino acid sequence shown as SEQ ID NO: 8 herein) or in Tsukamoto et al., 1988, (which amino acid sequence is shown in SEQ ID NO: 6 herein) or i) which displays at least 60% homology (identity), preferred at least 70%, more preferred at least 75%, even more preferred at least 80%, especially at least 85%, especially preferred at least 90%, especially at least 95%, even especially more preferred at least 97%, especially at least 99% homology with at least one of said amino acid sequences shown in SEQ ID NOS 1: or 2 or 3 or 4 or 5 or 6 or 7 or 8 and/or ii) displays immunological cross-reactivity with an antibody raised against one or more of said alpha-amylases, and/or iii) is encoded by a DNA sequence which hybridizes, under the low to very high stringency conditions (said conditions described below) to the DNA sequences encoding the above-specified alpha-amylases which are apparent from SEQ ID NOS: 9, 10, 11, 12, and 32, respectively, of the present application (which encodes the amino acid sequences shown in SEQ ID NOS: 1, 2, 3, 4, and 5 herein, respectively), from SEQ ID NO: 4 of WO 95/26397 (which DNA sequence, together with the stop codon TAA, is shown in SEQ ID NO: 13 herein and encodes the amino acid sequence shown in SEQ ID NO: 8 herein) and from SEQ ID NO: 5 of WO 95/26397 (shown in SEQ ID NO: 14 herein), respectively.

In connection with property i), the "homology" (identity) may be determined by use of any conventional algorithm, preferably by use of the gap programme from the GCG package version 8 (August 1994) using default values for gap penalties, i.e., a gap creation penalty of 3.0 and gap extension penalty of 0.1 (Genetic Computer Group (1991) Programme Manual for the GCG Package, version 8, 575 Science Drive, Madison, Wis., USA 53711).

The parent Termamyl-like alpha-amylase backbone may in an embodiment have an amino acid sequence which has a degree of identity to SEQ ID NO: 4 of at least 65%, preferably at least 70%, preferably at least 75%, more preferably at least 80%, more preferably at least 85%, even more preferably at least about 90%, even more preferably at least 95%, even more preferably at least 97%, and even more preferably at least 99% identity determined as described above A structural alignment between Termamyl® (SEQ ID NO: 4) and a Termamyl-like alpha-amylase may be used to identify equivalent/corresponding positions in other Termamyl-like alpha-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., 1987, *FEBS Letters* 224: 149-155) and reverse threading (Huber and Torda, 1998, *Protein Science* 7(1): 142-149.

For example, the corresponding positions, of target residues found in the C-domain of the *B. licheniformis* alpha-amylase, in the amino acid sequences of a number of Termamyl-like alpha-amylases which have already been mentioned are as follows:

| Termamyl-like alpha-amylase | | | | | |
|---|---|---|---|---|---|
| *B. lich.* (SEQ ID NO: 4) | S356 | Y358 | E376 | S417 | A420 |
| *B. amylo.* (SEQ ID NO: 5) | S356 | Y358 | E376 | S417 | A420 |
| *B. stearo.* (SEQ ID NO: 3) | — | Y361 | — | — | — |
| *Bac.* WO 95/26397 (SEQ ID NO: 2) | — | Y363 | — | S419 | — |
| *Bac.* WO 95/26397 (SEQ ID NO: 1) | — | Y363 | — | — | — |

As will be described further below mutations of these conserved amino acid residues are very important in relation to increasing the stability at acidic pH and/or at low calcium concentration at high temperatures.

Property ii) (see above) of the alpha-amylase, i.e., the immunological cross reactivity, may be assayed using an antibody raised against, or reactive with, at least one epitope of the relevant Termamyl-like alpha-amylase. The antibody, which may either be monoclonal or polyclonal, may be produced by methods known in the art, e.g., as described by Hudson et al., Practical Immunology, Third edition (1989), Blackwell Scientific Publications. The immunological cross-reactivity may be determined using assays known in the art, examples of which are Western Blotting or radial immunodiffusion assay, e.g., as described by Hudson et al., 1989. In this respect, immunological cross-reactivity between the alpha-amylases having the amino acid sequences SEQ ID NOS: 1, 2, 3, 4, 5, 6, 7, or 8 respectively, have been found.

The oligonucleotide probe used in the characterization of the Termamyl-like alpha-amylase in accordance with property iii) above may suitably be prepared on the basis of the full or partial nucleotide or amino acid sequence of the alpha-amylase in question.

Suitable conditions for testing hybridization involve presoaking in 5×SSC and prehybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at ~40° C., followed by three times washing of the filter in 2×SSC, 0.2% SDS at 40° C. for 30 minutes (low stringency), preferred at 50° C. (medium stringency), more preferably at 65° C. (high stringency), even more preferably at ~75° C. (very high stringency). More details about the hybridization method can be found in Sambrook et al., *Molecular Cloning: A Laboratory Manual*, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant which is the result of a modification (insertion, substitution, deletion) of one or more amino acid residues of the naturally occurring alpha-amylase.

Parent Hybrid Alpha-Amylases

The parent alpha-amylase (backbone) may be a hybrid alpha-amylase, i.e., an alpha-amylase which comprises a combination of partial amino acid sequences derived from at least two alpha-amylases.

The parent hybrid alpha-amylase may be one which on the basis of amino acid homology and/or immunological cross-reactivity and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase from which a partial amino acid sequence derives may, e.g., be any of those specific Termamyl-like alpha-amylase referred to herein.

For instance, the parent alpha-amylase may comprise a C-terminal part of an alpha-amylase derived from a strain of *B. licheniformis*, and a N-terminal part of an alpha-amylase derived from a strain of *B. amyloliquefaciens* or from a strain of *B. stearothermophilus*. For instance, the parent alpha-amylase may comprise at least 430 amino acid residues of the C-terminal part of the *B. licheniformis* alpha-amylase. A such hybrid Termamyl-like alpha-amylase may be identical to the Bacillus licheniformis alpha-amylase shown in SEQ ID NO: 4, except that the N-terminal 35 amino acid residues (of the mature protein) is replaced with the N-terminal 33 amino acid residues of the mature protein of the *Bacillus amyloliquefaciens* alpha-amylase (BAN) shown in SEQ ID NO: 5. A such hybrid may also consist of an amino acid segment corresponding to the 68 N-terminal amino acid residues of the *B. stearothermophilus* alpha-amylase having the amino acid sequence shown in SEQ ID NO: 3 and an amino acid segment corresponding to the 415 C-terminal amino acid residues of the *B. licheniformis* alpha-amylase having the amino acid sequence shown in SEQ ID NO: 4.

The non-Termamyl-like alpha-amylase may, e.g., be a fungal alpha-amylase, a mammalian or a plant alpha-amylase or a bacterial alpha-amylase (different from a Termamyl-like alpha-amylase). Specific examples of such alpha-amylases include the *Aspergillus oryzae* TAKA alpha-amylase, the *A. niger* acid alpha-amylase, the *Bacillus subtilis* alpha-amylase, the porcine pancreatic alpha-amylase and a barley alpha-amylase. All of these alpha-amylases have elucidated structures which are markedly different from the structure of a typical Termamyl-like alpha-amylase as referred to herein.

The fungal alpha-amylases mentioned above, i.e., derived from *A. niger* and *A. oryzae*, are highly homologous on the amino acid level and generally considered to belong to the same family of alpha-amylases. The fungal alpha-amylase derived from *Aspergillus oryzae* is commercially available under the tradename Fungamyl™.

Furthermore, when a particular variant of a Termamyl-like alpha-amylase (variant of the invention) is referred to—in a conventional manner—by reference to modification (e.g., deletion or substitution) of specific amino acid residues in the amino acid sequence of a specific Termamyl-like alpha-amylase, it is to be understood that variants of another Termamyl-like alpha-amylase modified in the equivalent position(s) (as determined from the best possible amino acid sequence alignment between the respective amino acid sequences) are encompassed thereby. A preferred embodiment of a variant of the invention is one derived from a *B. licheniformis* alpha-amylase (as parent Termamyl-like alpha-amylase), e.g., one of those referred to above, such as the *B. licheniformis* alpha-amylase having the amino acid sequence shown in SEQ ID NO: 4.

Altered Properties of Variants of the Invention

The following discusses the relationship between alterations/mutations which may be present in variants of the invention, and desirable alterations in properties (relative to those a parent, Termamyl-like alpha-amylase) which may result therefrom.

Increased Stability at Acidic pH and/or Low Calcium Concentration at High Temperatures The present invention relates to a variant of a parent Termamyl-like alpha-amylase, which variant alpha-amylase has been altered in comparison to the parent alpha-amylase in one or more solvent exposed amino acid residues on the surface of the alpha-amylase to increase the overall hydrophobicity of the alpha-amylase and/or to increase the overall numbers of methyl groups in the sidechains of said solvent exposed amino acid residues on the surface.

In a preferred embodiment one or more solvent exposed amino acid residues on a concave surface with inwards bend are altered to more hydrophobic amino acid residues.

In another preferred embodiment one or more solvent exposed amino acid residues on a convex surface are altered to increase the number of methyl groups in the sidechain.

The present invention relates to an alpha-amylase variant of a parent Termamyl-like alpha-amylase, comprising an alteration at one or more positions selected from the group of: E376, S417, A420, S356, Y358;
wherein (a) the alteration(s) are independently
(i) an insertion of an amino acid downstream of the amino acid which occupies the position,
(ii) a deletion of the amino acid which occupies the position, or
(iii) a substitution of the amino acid which occupies the position with a different amino acid,
(b) the variant has alpha-amylase activity and (c) each position corresponds to a position of the amino acid sequence of the parent Termamyl-like alpha-amylase having the amino acid sequence of SEQ ID NO: 4.

In an embodiment the alteration is one of the following substitutions: E376A,R,D,C,Q,G,H,I,K,L,M,N,F,P,S,T,W,Y,V.

In a preferred embodiment the substitution is: E376K.

In an embodiment the alteration is one of the following substitutions: S417A,R,D,C,E,Q,G,H,I,K,L,M,N,F,P,T,W,Y,V;

In a preferred embodiment the substitution is S417T.

In an embodiment the alteration is one of the following substitutions A420R,D,C,E,Q,G,H,I,K,L,M,N,F,P,S,T,W,Y,V;

In a preferred embodiment the substitution is: A420Q,R.

In an embodiment the alteration is one of the following substitutions: S356A,R,D,C,E,Q,G,H,I,K,L,M,N,F,P,T,W,Y,V.

In an embodiment the alteration is one of the following substitutions Y358A,R,D,C,E,Q,G,H,I,K,L,M,N,F,P,S,T,W,V.

In a preferred embodiment the substitution is Y358F.

In an embodiment of the invention a variant comprises one or more of the following substitutions: E376K, S417T, A420Q,R, S356A, Y358F.

The increase in stability at acidic pH and/or low calcium concentration at high temperatures may be determined using the method described below in Example 2 illustrating the invention.

The parent Termamyl-like alpha-amylase used as the backbone for preparing variants of the invention may be any Termamyl-like alpha-amylases as defined above.

Specifically contemplated are parent Termamyl-like alpha-amylases selected from the group derived from *B. licheniformis*, such as *B. licheniformis* strain ATCC 27811, *B. amyloliquefaciens*, *B. stearothermophilus*, *Bacillus* sp. NCIB 12289, NCIB 12512, NCIB 12513 or DSM 9375, and the parent Termamyl-like alpha-amylases depicted in SEQ ID NOS: 1, 2, 3, 4, 5, 6, 7 and 8.

In an embodiment of the invention the parent Termamyl-like alpha-amylase is a hybrid alpha-amylase being identical to the *Bacillus licheniformis* alpha-amylase shown in SEQ ID NO: 4 (Termamyl), except that the N-terminal 35 amino acid residues (of the mature protein) is replaced with the N-terminal 33 amino acid residues of the mature protein of the *Bacillus amyloliquefaciens* alpha-amylase (BAN) shown in SEQ ID NO: 5. The parent Termamyl-like hybrid alpha-amylase may be the above mentioned hybrid Termamyl-like alpha-amylase which further has the following mutations: H156Y+181T+190F+209V+264S (using the numbering in SEQ ID NO: 4). Said backbone is referred to below as "LE174".

The parent alpha-amylase may advantageously further have a mutation in one or more of the following positions: K176, I201 and H205 (using the numbering in SEQ ID NO: 4), especially one or more the following substitutions:

K176R, I201F, and H205N (using the numbering in SEQ ID NO: 4), such as specifically the following substitutions: K176R+I201F+H205N (using the numbering in SEQ ID NO: 4).

The inventors have found that the above mentioned variants have increased stability at pHs below 7.0 (i.e., acidic pH) and/or at calcium concentration below 1 mM (40 ppm) (i.e., low calcium concentrations) at temperatures in the range from 95 to 160° C. (i.e., high temperatures) relative to the parent Termamyl-like alpha-amylase.

Alterations (e.g., by substitution) of one or more solvent exposed amino acid residues which 1) increase the overall hydrophobicity of the enzyme, or 2) increase the number of methyl groups in the sidechains of the solvent exposed amino acid residues improve the temperature stability. It is preferred to alter (e.g., by substitution) to more hydrophobic residues on a concave surface with inwards bend. On a convex surface alterations (e.g., by substitution) to amino acid residues with an increased number of methyl groups in the sidechain are preferred.

Using the program CAST found on the internet at sunrise.cbs.umn.edu/cast/ version 1.0 (release February 1998) (reference: Liang et al., 1998, Anatomy of protein Pockets and Cavities: Measurements of binding site geometry and implications for ligand design. *Protein Science* 7: 1884-1897), a concave area which access to the surface can be identified. Access to the surface is in the program defined as a probe with a diameter of 1.4 Å can pass in and out. Using default parameters in the CAST program concave cavities can be found using the Calcium depleted alpha-amylase structure from *B. licheniformis* as found in the Brookhaven database (1BPL):

Three types of interaction can be rationalized:
A. Interaction between the sidechain of the residue and the protein,
B. Interaction between the sidechain of the residue and the surrounding water,
C. Interaction between the water and the protein.

Using the parent Termamyl-like alpha-amylase shown in SEQ ID NO: 4 as the backbone the following positions are considered to be solvent exposed and may suitably be altered: E376, S417, A420, S356, Y358.

Corresponding and other solvent exposed positions on the surface of other Termamyl-like alpha-amylase may be identified using the dssp program by Kabsch and Sander, 1983, *Biopolymers* 22: 2577-2637. The convex surfaces can be identified using the AACAVI program part from the WHATIF package (Vriend, 1990, Whatif and drug design program. *J. Mol. Graph.* 8: 52-56. version 19980317).

In an embodiment of the invention a variant comprises one or more of the following substitutions: E376K, S417T, A420Q,R, S356A, Y358F.

The inventors have found that the stability at acidic pH and/or low calcium concentration at high temperatures may be increased even more by combining mutations in the above mentioned positions, i.e., E376, S417, A420, S356, Y358, (using the SEQ ID NO: 4 numbering) with mutations in one or more of positions K176, I201, and H205.

The following additional substitutions are preferred:
K176A,R,D,C,E,Q,G,H,I,L,M,N,F,P,S,T,W,Y,V;
I201A,R,D,C,E,Q,G,H,L,K,M,N,F,P,S,T,W,Y,V;
H205A,R,D,C,E,Q,G,I,L,K,M,N,F,P,S,T,W,Y,V;

As also shown in Example 2 illustrating the invention combining the following mutations give increased stability:
K176+I201F+H205N+E376K+A420R or
K176+I201F+H205N+S417T+A420Q or
K176+I201F+H205N+S356A+Y358F using the hybrid alpha-amylase referred to as LE174 as the parent Termamyl-like alpha-amylase.

General Mutations in Variants of the Invention

It may be preferred that a variant of the invention comprises one or more modifications in addition to those outlined above. Thus, it may be advantageous that one or more proline residues present in the part of the alpha-amylase variant which is modified is/are replaced with a non-proline residue which may be any of the possible, naturally occurring non-proline residues, and which preferably is an alanine, glycine, serine, threonine, valine or leucine.

Analogously, it may be preferred that one or more cysteine residues present among the amino acid residues with which the parent alpha-amylase is modified is/are replaced with a non-cysteine residue such as serine, alanine, threonine, glycine, valine or leucine.

Furthermore, a variant of the invention may—either as the only modification or in combination with any of the above outlined modifications—be modified so that one or more Asp and/or Glu present in an amino acid fragment corresponding to the amino acid fragment 185-209 of SEQ ID NO: 4 is replaced by an Asn and/or Gln, respectively. Also of interest is the replacement, in the Termamyl-like alpha-amylase, of one or more of the Lys residues present in an amino acid fragment corresponding to the amino acid fragment 185-209 of SEQ ID NO: 4 by an Arg.

It will be understood that the present invention encompasses variants incorporating two or more of the above outlined modifications.

Furthermore, it may be advantageous to introduce point-mutations in any of the variants described herein.

Cloning a DNA Sequence Encoding an Alpha-Amylase of the Invention

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labelled oligonucleotide probes may be synthesized and used to identify alpha-amylase-encoding clones from a genomic library prepared from the organism in question. Alternatively, a labelled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., the phosphoroamidite method described by Beaucage and Caruthers (1981), or the method described by Matthes et al. (1984). In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or Saiki et al. (1988).

Site-Directed Mutagenesis

Once an alpha-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localised or region-specific random mutagenesis in at least three parts of the gene translating to the amino acid sequence shown in question, or within the whole gene.

The random mutagenesis of a DNA sequence encoding a parent alpha-amylase may be conveniently performed by use of any method known in the art.

In relation to the above, a further aspect of the present invention relates to a method for generating a variant of a parent alpha-amylase, e.g., wherein the variant exhibits altered or increased thermal stability relative to the parent, the method comprising:

(a) subjecting a DNA sequence encoding the parent alpha-amylase to random mutagenesis, (b) expressing the mutated DNA sequence obtained in step (a) in a host cell, and (c) screening for host cells expressing an alpha-amylase variant which has an altered property (i.e., thermal stability) relative to the parent alpha-amylase.

Step (a) of the above method of the invention is preferably performed using doped primers.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the alpha-amylase enzyme by any published technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program which, inter alia, ensures that introduction of stop codons is avoided.

When PCR-generated mutagenesis is used, either a chemically treated or non-treated gene encoding a parent alpha-amylase is subjected to PCR under conditions that increase the mis-incorporation of nucleotides (Deshler 1992; Leung et al., Technique, Vol. 1, 1989, pp. 11-15).

A mutator strain of *E. coli* (Fowler et al., 1974, *Molec. Gen. Genet.* 133: 179-191), *S. cereviseae* or any other microbial organism may be used for the random mutagenesis of the DNA encoding the alpha-amylase by, e.g., transforming a plasmid containing the parent glycosylase into the mutator strain, growing the mutator strain with the plasmid and isolating the mutated plasmid from the mutator strain. The mutated plasmid may be subsequently transformed into the expression organism.

The DNA sequence to be mutagenized may be conveniently present in a genomic or cDNA library prepared from an organism expressing the parent alpha-amylase. Alternatively, the DNA sequence may be present on a suitable vector such as a plasmid or a bacteriophage, which as such may be incubated with or other-wise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram-negative bacteria such as *E. coli*.

The mutated DNA sequence may further comprise a DNA sequence encoding functions permitting expression of the mutated DNA sequence.

Localized Random Mutagenesis

The random mutagenesis may be advantageously localized to a part of the parent alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative Methods of Providing Alpha-Amylase Variants

Alternative methods for providing variants of the invention include gene shuffling method known in the art including the methods, e.g., described in WO 95/22625 (from Affymax Technologies N.V.) and WO 96/00343 (from Novo Nordisk NS).

Expression of Alpha-Amylase Variants of the Invention

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al., *Molecular Cloning: A Laboratory Manual*, 2nd Ed., Cold Spring Harbor, 1989).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gram-negative bacteria such as *E. coli*. The transformation of the bacteria may, for instance, be effected by protoplast transformation or by using competent cells in a manner known per se.

The yeast organism may favourably be selected from a species of *Saccharomyces* or *Schizosaccharomyces,* e.g., *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238023.

In a yet further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The alpha-amylase variants of this invention possess valuable properties allowing for a variety of industrial applications. An enzyme variant of the invention is applicable as a component in washing, dishwashing and hard-surface cleaning detergent compositions. Numerous variants are particularly useful in the production of sweeteners and ethanol from starch, and/or for textile desizing. Conditions for conventional starch-conversion processes, including starch liquefaction and/or saccharification processes, are described in, e.g., U.S. Pat. No. 3,912,590 and in EP patent publications Nos. 252,730 and 63,909.

Production of Sweeteners from Starch:

A "traditional" process for conversion of starch to fructose syrups normally consists of three consecutive enzymatic processes, viz. a liquefaction process followed by a saccharification process and an isomerization process. During the liquefaction process, starch is degraded to dextrins by an alpha-amylase (e.g., Termamyl™) at pH values between 5.5 and 6.2 and at temperatures of 95-160° C. for a period of approx. 2 hours. In order to ensure an optimal enzyme stability under these conditions, 1 mM of calcium is added (40 ppm free calcium ions).

After the liquefaction process the dextrins are converted into dextrose by addition of a glucoamylase (e.g., AMG™) and a debranching enzyme, such as an isoamylase or a pullulanase (e.g., Promozyme™). Before this step the pH is reduced to a value below 4.5, maintaining the high temperature (above 95° C.), and the liquefying alpha-amylase activity is denatured. The temperature is lowered to 60° C., and glucoamylase and debranching enzyme are added. The saccharification process proceeds for 24-72 hours.

After the saccharification process the pH is increased to a value in the range of 6-8, preferably pH 7.5, and the calcium is removed by ion exchange. The dextrose syrup is then converted into high fructose syrup using, e.g., an immmobilized glucose isomerase (such as Sweetzyme™).

At least 1 enzymatic improvement of this process could be envisaged. Reduction of the calcium dependency of the liquefying alpha-amylase. Addition of free calcium is required to ensure adequately high stability of the alpha-amylase, but free calcium strongly inhibits the activity of the glucose isomerase and needs to be removed, by means of an expensive unit operation, to an extent which reduces the level of free calcium to below 3-5 ppm. Cost savings could be obtained if such an operation could be avoided and the liquefaction process could be performed without addition of free calcium ions.

To achieve that, a less calcium-dependent Termamyl-like alpha-amylase which is stable and highly active at low concentrations of free calcium (<40 ppm) is required. Such a Termamyl-like alpha-amylase should have a pH optimum at a pH in the range of 4.5-6.5, preferably in the range of 4.5-5.5.

Detergent Compositions

As mentioned above, variants of the invention may suitably be incorporated in detergent compositions. Reference is made, for example, to WO 96/23874 and WO 97/07202 for further details concerning relevant ingredients of detergent compositions (such as laundry or dishwashing detergents), appropriate methods of formulating the variants in such detergent compositions, and for examples of relevant types of detergent compositions.

Detergent compositions comprising a variant of the invention may additionally comprise one or more other enzymes, such as a lipase, cutinase, protease, cellulase, peroxidase or laccase, and/or another alpha-amylase.

Alpha-amylase variants of the invention may be incorporated in detergents at conventionally employed concentrations. It is at present contemplated that a variant of the invention may be incorporated in an amount corresponding to 0.00001-1 mg (calculated as pure, active enzyme protein) of alpha-amylase per liter of wash/dishwash liquor using conventional dosing levels of detergent.

Materials and Methods

Enzymes:

LE174 hybrid alpha-amylase variant: LE174 is a hybrid Termamyl-like alpha-amylase being identical to the Termamyl sequence, i.e., the *Bacillus licheniformis* alpha-amylase shown in SEQ ID NO: 4, except that the N-terminal 35 amino acid residues (of the mature protein) has been replaced by the N-terminal 33 residues of BAN (mature protein), i.e., the *Bacillus amyloliquefaciens* alpha-amylase shown in SEQ ID NO: 5, which further have following mutations: H156Y+A181T+N190F+A209V+Q264S (using the numbering in SEQ ID NO: 4).

Construction of pSNK101

This *E. coli/Bacillus* shuttle vector can be used to introduce mutations without expression of alpha-amylase in *E. coli* and then be modified in such way that the alpha-amylase is active in *Bacillus*. The vector was constructed as follows: The alpha-amylase gene in the pX vector (pDN1528 with the following alterations within amyL: BAN(1-33), H156Y, A181T, N190F, A209V, Q264S, the plasmid pDN1528 is further described in Example 1) was inactivated by interruption in the PstI site in the 5"coding region of the alpha-amylase gene by a 1.2 kb fragment containing an *E. coli* origin fragment. This fragment was amplified from the pUC19 (GenBank Accession #:X02514) using the forward primer 1: 5"-gacctgcagt-caggcaacta-3" (SEQ ID NO: 27) and the reverse primer 1: 5"-tagagtcgacctgcaggcat-3" (SEQ ID NO: 28). The PCR amplicon and the pX plasmid containing the alpha-amylase gene were digested with PstI at 37° C. for 2 hours. The pX vector fragment and the *E. coli* origin amplicon were ligated at room temperature, for 1 hour and transformed in *E. coli* by electrotransformation. The resulting vector is designated pSnK101.

This *E. coli*/Bacillus shuttle vector can be used to introduce mutations without expression of alpha-amylase in *E. coli* and then be modified in such way that the alpha-amylase is active in *Bacillus*. The vector was constructed as follows: The alpha-amylase gene in the pX vector (pDN1528 with the following alterations within amyL: BAN(1-33), H156Y+A181T+N190F+A209V+Q264S, the plasmid pDN1528 is further described in Example 1) was inactivated by interruption in the PstI site in the 5"coding region of the alpha-amylase gene by a 1.2 kb fragment containing an *E. coli* origin fragment. This fragment was amplified from the pUC19 (GenBank Accession #:X02514) using the forward primer 2: 5"-gacctgcagt-caggcaacta-3" (SEQ ID NO: 29) and the reverse primer 2: 5"-tagagtcgacctgcaggcat-3" (SEQ ID NO: 30). The PCR amplicon and the pX plasmid containing the alpha-amylase gene were digested with PstI at 37° C. for 2 hours. The pX vector fragment and the *E. coli* origin amplicon were ligated at room temperature for 1 hour and transformed in *E. coli* by electrotransformation. The resulting vector is designated pSnK101.

Low pH Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with 10 micrograms/ml chloramphenicol at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with citrate buffer, pH 4.5 and incubated at 90° C. for 15 min. The cellulose acetate filters with colonies are stored on the TY-plates at room temperature until use. After incubation, residual activity is detected on assay plates containing 1% agarose, 0.2% starch in citrate buffer, pH 6.0. The assay plates with nitrocellulose filters are marked the same way as the filter sandwich and incubated for 2 hours at 50° C. After removal of the filters the assay plates are stained with 10% Lugol solution. Starch degrading variants are detected as white spots on dark blue background and then identified on the storage plates. Positive variants are rescreened twice under the same conditions as the first screen.

Secondary Screening

Positive transformants after rescreening are picked from the storage plate and tested in a secondary plate assay. Positive transformants are grown for 22 hours at 37° C. in 5 ml LB+chloramphenicol. The *Bacillus* culture of each positive transformant and a control LE174 variant were incubated in citrate buffer, pH 4.5 at 90° C. and samples were taken at 0, 10, 20, 30, 40, 60 and 80 minutes. A 3 microliter sample was spotted on a assay plate. The assay plate was stained with 10% Lugol solution. Improved variants were seen as variants with higher residual activity detected as halos on the assay plate than the backbone. The improved variants are determined by nucleotide sequencing.

Fermentation and Purification of Alpha-Amylase Variants

A *B. subtilis* strain harbouring the relevant expression plasmid is streaked on a LB-agar plate with 15 µg/ml chloramphenicol from −80° C. stock, and grown overnight at 37° C.

The colonies are transferred to 100 ml BPX media supplemented with 15 micrograms/ml chloramphenicol in a 500 ml shaking flask.

Composition of BPX Medium:

| | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| Na$_2$HPO$_4$, 12 H$_2$O | 9 g/l |
| Pluronic ™ | 0.1 g/l |

The culture is shaken at 37° C. at 270 rpm for 5 days.

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10000 cut off membrane) and the buffer is changed to 20 mM Acetate pH 5.5. The UF-filtrate is applied on an S-sepharose F.F. and elution is carried out by step elution with 0.2 M NaCl in the same buffer. The eluate is dialysed against 10 mM Tris, pH 9.0 and applied on a Q-sepharose F.F. and eluted with a linear gradient from 0-0.3M NaCl over 6 column volumes. The fractions which contain the activity (measured by the Phadebas assay) are pooled, pH was adjusted to pH 7.5 and remaining color was removed by a treatment with 0.5% W/vol. active coal in 5 minutes.

Stability Determination

All the stability trials are made using the same set up. The method is:

The enzyme is incubated under the relevant conditions (1-4). Samples are taken at 0, 5, 10, 15 and 30 minutes and diluted 25 times (same dilution for all taken samples) in assay buffer (0.1 M 50 mM Britton buffer pH 7.3) and the activity is measured using the Phadebas assay (Pharmacia) under standard conditions pH 7.3, 37° C.

The activity measured before incubation (0 minutes) is used as reference (100%). The decline in percent is calculated as a function of the incubation time. The table shows the residual activity after 30 minutes of incubation.

Activity Determination—(KNU)

One Kilo alpha-amylase Unit (1 KNU) is the amount of enzyme which breaks down 5.26 g starch (Merck, Amylum Solubile, Erg. B 6, Batch 9947275) per hour in Novo Nordisk's standard method for determination of alpha-amylase based upon the following condition:

| | |
|---|---|
| Substrate | soluble starch |
| Calcium content in solvent | 0.0043M |
| Reaction time | 7-20 minutes |
| Temperature | 37° C. |
| pH | 5.6 |

Detailed description of Novo Nordisk's analytical method (AF 9) is available on request.

Specific Activity Determination

Assay for Alpha-Amylase Activity

Alpha-amylase activity is determined by a method employing Phadebas® tablets as substrate. Phadebas tablets (Phadebas® Amylase Test, supplied by Pharmacia Diagnostic) contain a cross-linked insoluble blue-coloured starch polymer which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolysed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyse a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

EXAMPLES

Example 1

Construction, by Random Mutagenesis, of Termamyl-like LE174 Alpha-Amylase Variants Having an Improved Stability at Low pH and a Reduced Dependency on Calcium Ions for Stability Compared to the Parent Enzyme Random Mutagenesis To improve the stability at low pH and low calcium concentration of the parent LE174 alpha-amylase variant random mutagenesis in preselected regions was performed.

The regions were:

| Region: | Residue: |
|---|---|
| SERI | A425-Y438 |
| SERII | W411-L424 |
| SERIII | G397-G410 |
| SERV | T369-H382 |
| SERVII | G310-F323 |
| SERIX | L346-P359 |

For each six region, random oligonucleotides are synthesized using the same mutation rate (97% backbone and 1% of each of the three remaining nucleotides giving 3% mutations) in each nucleotide position in the above regions, e.g., 1. position in condon for A425: 97% C, 1% A, 1% T, 1% G. The six random oligonucleotides and if used complementary SOE helping primers are shown in tables 1-6: with the four distribution of nucleotides below.

TABLE 1

RSERI:

5'-GC GTT TTG CCG GCC GAC ATA 312 234 322 243 333 133 444 233 423 242 212

211 243 343 CAA ACC TGA ATT-3'
(SEQ ID NO: 15)

TABLE 2

RSERII:

5'-GC GTT TTG CCG GCC GAC ATA CAT TCG CTT TGC CCC ACC GGG TCC GTC

TGT TAT TAA TGC CGC 311 133 241 122 243 113 341 432 423 433 223 332

242 331 GCC GAC AAT GTC ATG GTG-3'
(SEQ ID NO: 16)

TABLE 3

RSERIII:

5'-GTC GCC TTC CCT TGT CCA 433 413 112 423 124 424 423 411 121 123 124 324

243 233 GTA CGC ATA CTG TTT TCT-3'
(SEQ ID NO: 17)

Helping primer FSERIII:

5'-TGG ACA AGG GAA GGC GAC AG-3'
(SEQ ID NO: 18)

TABLE 4

RSERV:

5-TAA GAT CGG TTC AAT TTT 424 222 311 443 144 112 223 434 324 441 423 233

222 342 CCC GTA CAT ATC CCC GTA GAA-3
(SEQ ID NO: 19)

Helping primer FSERV:

5-AAA ATT GAA CCG ATC TTA-3
(SEQ ID NO: 20)

TABLE 5

FSERVII:

5'-TT CCA TGC TGC ATC GAC ACA GGG AGG CGG CTA TGA TAT GAG GAA ATT

GCT GAA 344 213 442 342 223 311 431 233 422 411 123 442 213 122

TGT CGA TAA CCA-3'
(SEQ ID NO: 21)

Helping primer RSERVII:

5'- TGT CGA TGC AGC ATG GAA -3'
(SEQ ID NO: 22)

TABLE 6

FSERIX:

5'-GT CCA AAC ATG GTT TAA GCC 432 243 221 343 222 212 232 313 114 441 123

244 121 333 TCA GGT TTT CTA CGG GGA-3'
(SEQ ID NO: 23)

Helping primer RSERIX:

5'-GGC TTA AAC CAT GTT TGG AC-3'
(SEQ ID NO: 24)

Distribution of Nucleotides in Each Mutated Nucleotide Position

1: 97% A, 1% T, 1% C, 1% G
2: 97% T, 1% A, 1% C, 1% G
3: 97% C, 1% A, 1% T, 1% G
4: 97% G, 1% A, 1% T, 1% C

Construction of Plasmid Libraries

Two approximately 1.4 kb fragments were PCR amplified using the primer 1B: 5'-CGA TTG CTG ACG CTG TTA TTT GCG-3' (SEQ ID NO: 25) and the random oligonucleotide apparent from table 1, respectively the random oligonucleotide apparent from table 2. The vector pSnK101 and the PCR fragments were digested with EcoRV and Eagl for 2 hours. The approximately 3.6 kb vector fragment and the approximately 1.3 kb PCR fragments was purified and ligated overnight and transformed in to *E. coli* and then further transformed into a *Bacillus* host strain as described below. The random oligonucleotides apparent from Tables 3-6 (which by a common term is designated aSER and bSER in FIG. 2) for each region and specific *B. licheniformis* primers 1B (SEQ ID NO: 25) and #63: 5'-CTA TCT TTG AAC ATA AAT TGA AAC C-3' (SEQ ID NO: 26) covering the EcoRV and the EagI sites in the LE174 sequence are used to generate PCR-library-fragments by the overlap extension method (Horton et al., 1989, Gene 77: 61-68) FIG. 2 shows the PCR strategy. The PCR fragments are cloned in the E. coli/Bacillus shuttle vector pSNK101 (see Materials and Methods) enabling mutagenesis in E. coli and immediate expression in Bacillus subtilis preventing lethal accumulation of amylases in E. coli. After establishing the cloned PCR fragments in E. coli, a modified pUC19 fragment is digested out of the plasmid and the promoter and the mutated Termamyl gene is physically connected and expression can take place in the Bacillus host.

Screening

The six libraries were screened in the low pH filter assays described in the "Material and Methods" section above.

All variants listed in the table in Example 2 below was prepared as described in Example 1.

Example 2

Measurement of Stability

Normally, industrial liquefaction processes is run at pH 6.0-6.2 with addition of about 40 ppm free calcium in order to improve the stability at 95° C.-105° C. Variants of the invention have been made in order to improve the stability at:
1. lower pH than pH 6.2 and/or
2. at free calcium levels lower than 40 ppm free calcium.

An assay which measures the stability at acidic pH, pH 5.0, in the presence of 5 ppm free calcium was used to measure the increase in stability.

10 micrograms of the variant was incubated under the following conditions: A 0.1 M acetate solution, pH adjusted to pH 5.0, containing 5 ppm calcium and 5% w/w common corn starch (free of calcium). Incubation was made in a water bath at 95° C. for 30 minutes.

Results:
Increased stability at pH 5.0, 5 ppm calcium incubated at 95° C.

| Minutes of Incubation | LE174 with K176R + I201F + H205N | LE174 with K176R + I201F + H205N + E376K + A420R | LE174 with WITH K176R + I201F + H205N + S417T + A420Q | LE174 with K176R + I201F + H205N + S356A + Y358F |
|---|---|---|---|---|
| 0 | 100 | 100 | 100 | 100 |
| 5 | 65 | 61 | 66 | 66 |
| 10 | 58 | 53 | 60 | 59 |
| 15 | 51 | 48 | 55 | 56 |
| 30 | 36 | 39 | 45 | 49 |

Specific Activity Determination.

The specific activity was determined using the Phadebas assay (Pharmacia) (described above) as activity/mg enzyme. The activity was determined using the alpha-amylase assay described in the Materials and Methods section herein.
LE174 with the following substitutions: K176R+I201F+H205N
Specific activity determined: 13,400 NU/mg
LE174 with the following substitutions: K176R+I201F+H205N+E376K+A420R:
Specific activity determined: 14,770 NU/mg
LE174 with the following substitutions: K176R+I201F+H205N+S417T+A420Q:
Specific activity determined: 16,670 NU/mg
LE174 with the following substitutions: K176R+I201F+H205N+S356A+Y358F:
Specific activity determined: 15,300 NU/mg

REFERENCES CITED

Klein et al., Biochemistry, 31, 8740-8746 (1984),
Mizuno et al., J. Mol. Biol. 234, 1282-1283 (1993),
Chang et al, J. Mol. Biol. 229, 235-238 (1993),
Larson, J. Mol. Biol. 235, 1560-1584 (1994),
Lawson, J. Mol. Biol. 236, 590-600 (1994),
Qian et al., J. Mol. Biol. 231, 785-799 (1993),
Brady et al., Acta Crystallogr. sect. B, Vol. 47, pp. 527-535 (1991),
Swift et al., Acta Crystallogr. sect. B, Vol. 47, pp. 535-544 (1988)
Kadziola, Ph.D. Thesis: "An alpha-amylase from Barley and its Complex with a Substrate Analogue Inhibitor Studied by X-ray Crystallography", Department of Chemistry University of Copenhagen 1993
MacGregor, Food Hydrocolloids, Vol. 1, No. 5-6, pp. 407-411 (1987)
Diderichsen and Christiansen, Cloning of a maltogenic alpha-amylase from Bacillus stearothermophilus, FEMS Microbiol. Letters, Vol. 56, pp. 53-60 (1988)
Hudson et al., Practical Immunology, Third edition (1989), Blackwell Scientific Publications,
Sambrook et al., Molecular Cloning: A Laboratory Manual, 2nd Ed., Cold Spring Harbor (1989),
Beaucage and Caruthers, Tetrahedron Letters, Vol. 22, pp. 1859-1869 (1981),
Matthes et al., The EMBO J., Vol. 3, pp. 801-805 (1984),
Saiki et al., Science, Vol. 239, pp. 487-491 (1988),
Morinaga et al., Biotechnology, Vol. 2, pp. 646-639 (1984),
Nelson and Long, Analytical Biochemistry, Vol. 180, pp. 147-151 (1989),
Hunkapiller et al., Nature, Vol. 310, pp. 105-111 (1984),
Higuchi, Krummel, and Saiki, A general method of in vitro preparation and specific mutagenesis of DNA fragments: study of protein and DNA interactions. Nucl. Acids Res. Vol. 16, pp. 7351-7367 (1988)
Dubnau et al., J. Mol. Biol., Vol. 56, pp. 209-221 (1971),
Gryczan et al., J. Bacteriol., Vol. 134, pp. 318-329 (1978),
Erlich, Proc. Natl. Acad. Sci., Vol. 74, pp. 1680-1682 (1977),
Boel et al., Biochemistry, Vol. 29, pp. 6244-6249 (1990).

The invention claimed is:

1. A variant alpha-amylase, said variant has an amino acid sequence which is at least 90% identical to SEQ ID NO: 3, has alpha-amylase activity and comprises an insertion at a position corresponding to position 376 of SEQ ID NO:4.

2. The variant of claim 1, wherein the variant has an amino acid sequence which is at least 95% identical to SEQ ID NO: 3.

3. The variant of claim 1, wherein the variant has an amino acid sequence which is at least 97% identical to SEQ ID NO: 3.

4. The variant of claim 1, wherein the variant has an amino acid sequence which is at least 99% identical to SEQ ID NO: 3.

5. A detergent composition comprising the variant alpha-amylase of claim 1 and surfactant.

6. A detergent composition of claim 5, further comprising an enzyme selected from the group consisting of a protease, a lipase, a peroxidase, another amylolytic enzyme, a cellulase, and combinations of any of the foregoing.

* * * * *